US011701453B2

(12) United States Patent
Bertassoni et al.

(10) Patent No.: US 11,701,453 B2
(45) Date of Patent: Jul. 18, 2023

(54) DENTAL PULP CONSTRUCT

(71) Applicant: OREGON HEALTH & SCIENCE UNIVERSITY, Portland, OR (US)

(72) Inventors: Luiz Bertassoni, Portland, OR (US); Anthony Tahayeri, Sherwood, OR (US); Avathamsa Athirasala, Hillsboro, OR (US); Jack L. Ferracane, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 736 days.

(21) Appl. No.: 16/618,329

(22) PCT Filed: May 30, 2018

(86) PCT No.: PCT/US2018/035200
§ 371 (c)(1),
(2) Date: Nov. 29, 2019

(87) PCT Pub. No.: WO2018/222761
PCT Pub. Date: Dec. 6, 2018

(65) Prior Publication Data
US 2021/0283311 A1 Sep. 16, 2021

Related U.S. Application Data

(60) Provisional application No. 62/512,675, filed on May 30, 2017.

(51) Int. Cl.
*A61L 27/52* (2006.01)
*A61L 27/12* (2006.01)
*A61L 27/22* (2006.01)
*C08L 89/06* (2006.01)
*A61L 27/54* (2006.01)
*C08L 93/00* (2006.01)

(52) U.S. Cl.
CPC .............. *A61L 27/52* (2013.01); *A61L 27/12* (2013.01); *A61L 27/222* (2013.01); *A61L 27/54* (2013.01); *C08L 89/06* (2013.01); *A61L 2400/06* (2013.01); *A61L 2430/12* (2013.01); *C08L 93/00* (2013.01)

(58) Field of Classification Search
CPC ..... A61C 5/50; A61C 8/0016; A61L 2400/06; A61L 27/52
See application file for complete search history.

(56) References Cited

U.S. PATENT DOCUMENTS

| | | | |
|---|---|---|---|
| 7,306,459 B1 | 12/2007 | Williams et al. | |
| 2005/0079470 A1 | 4/2005 | Rutherford et al. | |
| 2007/0092856 A1 | 4/2007 | Chow et al. | |
| 2009/0105193 A1* | 4/2009 | Prestwich | C07K 1/1072 514/54 |
| 2010/0233649 A1* | 9/2010 | McPeek | A61C 1/07 433/86 |
| 2014/0302111 A1 | 10/2014 | Mao et al. | |
| 2015/0147718 A1* | 5/2015 | Khakpour | A61C 5/62 433/81 |
| 2015/0250922 A1* | 9/2015 | Cole | A61K 47/10 604/20 |
| 2020/0306143 A1* | 10/2020 | Yelick | A61L 27/222 |

FOREIGN PATENT DOCUMENTS

| | | |
|---|---|---|
| DE | 102014201786 A1 | 8/2015 |
| WO | 2006116530 A2 | 11/2006 |

OTHER PUBLICATIONS

Strassler (Inside Dentistry, Mar. 2007, vol. 3, Fiber Posts: A clinical update) (Year: 2007).*
Annabi et al.: "25th Anniversary Article: Rational Design and Applications of Hydrogels in Regenerative Medicine", Advanced Materials, vol. 26, Jan. 8, 2014, 40 pages.
Athirasala et al.: "A Novel Strategy to Engineer Pre-Vascularized Full-Length Dental Pulp-Like Tissue Constructs", Scientific Reports, vol. 7, No. 1, Jun. 12, 2017, 11 pages.
Bertassoni et al.: "Direct-Write Bioprinting of Cell-Laden Methacrylated Gelatin Hydrogels", Biofabrication, vol. 6, Apr. 3, 2014, 12 pages.
Bertassoni et al.: "Hydrogel Bioprinted Microchannel Networks for Vascularization of Tissue Engineering Constructs", Lab Chip, vol. 14, No. 13, Jul. 7, 2014, 19 pages.
Dissanayaka et al.: "The Interplay of Dental Pulp Stem Cells and Endothelial Cells in an Injectable Peptide Hydrogel on Angiogenesis and Pulp Regeneration In Vivo", Tissue Engineering: Part A, vol. 21 Nos. 3 and 4, Oct. 10, 2014, 14 pages.
Duchi et al.: "Handheld Co-Axial Bioprinting: Application to In Situ Surgical Cartilage Repair", Scentific Reports, vol. 7, No. 5837, Jul. 19, 2017, 12 pages.
Galler et al.: "A Customized Self-Assembling Peptide Hydrogel for Dental Pulp Tissue Engineering", Tissue Engineering: Part A, vol. 18, Nos. 1 and 2, Sep. 27, 2011, 9 pages.
International Search Report and Written Opinion for International Application No. PCT/US2018/035200, dated Aug. 3, 2018, 6 pages.
Jimenez et al.: "Self-Assembling Peptide Nano Fibrous Hydrogel Scaffold (PuramatrixTM) in Regenerative Endodontics", EC Dental Science, vol. 2.5, Oct. 19, 2015, 9 pages.
Jones et al.: "An Optimized Injectable Hydrogel Scaffold Supports Human Dental Pulp Stem Cell Viability and Spreading", Advances in Medicine, vol. 2016, article 7363579, Apr. 11, 2016, 9 pages.

(Continued)

Primary Examiner — Mark V Stevens
(74) Attorney, Agent, or Firm — Stoel Rives LLP

(57) ABSTRACT

Disclosed is a method for filling a root canal in a tooth. The method includes positioning a fiber in the root canal of the tooth, filling at least a portion of the root canal with an unset hydrogel composition, such that the unset hydrogel composition contacts at least a portion of the fiber, setting the hydrogel composition, thereby forming a set hydrogel, and removing the fiber from the set hydrogel, thereby leaving a channel in the set hydrogel. Methods and kits for repairing teeth are also described.

19 Claims, 25 Drawing Sheets

(56) References Cited

OTHER PUBLICATIONS

Khayat et al.: "GelMA-Encapsulated hDPSCs and HUVECs for Dental Pulp Regeneration", Journal of Dental Research, vol. 96, No. 2, Dec. 15, 2016, 8 pages.
Komabayashi et al.: "Preliminary Study of Light-Cured Hydrogel for Endodontic Drug Delivery Vehicle", Journal of Investigative and Clinical Dentistry, vol. 7, Feb. 8, 2016, 6 pages.
Lim et al.: "New Visible-Light Photoinitiating System for Improved Print Fidelity in Gelatin-Based Bioinks", ACS Biomaterials Science & Engineering, vol. 2, Aug. 1, 2016, 11 pages.
Lins et al.: "Matrix Stiffness Influences Odontoblast Progenitors and Endothelial Cell Response in 3D Microenvironments", AADR/CADR Annual Meeting, poster No. 1940, Mar. 19, 2016, 1 page.
Moinzadeh: "Contemporary Root Canal Filling Strategies", University of Amsterdam, Nov. 5, 2016, 15 pages.
Monteiro et al.: "Photopolymerization of Cell-Laden Gelatin Methacryloyl Hydrogels Using a Dental Curing Light for Regenerative Dentistry", Dental Materials, vol. 34, Dec. 6, 2017, 11 pages.
Nuti et al.: "Multipotent Differentiation of Human Dental Pulp Stem Cells: a Literature Review", Stem Cell Reviews and Reports, vol. 12, May 30, 2016, 13 pages.
Prateepchinda et al.: "Effect of Seeding Density on Human Dental Pulp Cell Response in Polyethylene Glycol-Fibrinogen Hydrogel", Society for Biomaterials, abstract No. 587, 2013, 1 page.
Prateepchinda: "Bioactive Hydrogel Scaffold for Guided Dental Pulp Regeneration", Columbia University, May 12, 2015, 191 pages.
Rosa et al.: "Dental Pulp Tissue Engineering in Full-Length Human Root Canals", Journal of Dental Research, vol. 92, No. 11, Sep. 20, 2013, 6 pages.
Ruangsawasdi et al.: "Fibrin Gel Improves Tissue Ingrowth and Cell Differentiation in Human Immature Premolars Implanted in Rats", Journal of Endodontics, vol. 40, No. 2, Oct. 25, 2013, 6 pages.
Sharma et al.: "Healing Response of Rat Pulp Treated with an Injectable Keratin Hydrogel", J Appl Biomater Funct Mater, vol. 15, No. 3, Apr. 20, 2017, 7 pages.
Yue et al.: "Synthesis, Properties, and Biomedical Applications of Gelatin Methacryloyl (GelMA) Hydrogels", Biomaterials, vol. 73, Aug. 28, 2015, 18 pages.
Macedo, et al.,"A Novel Methodology Providing Insights into Removal of Biofilm-Mimicking Hydrogel from Lateral Morphological Features of the Root Canal During Irrigation Procedures", International Endodontic Journal, vol. 47, Jan. 7, 2014, 12 pages.
European Patent Office, Extended European Search Report for Application 18808633.4, dated Jan. 14, 2021, 12 pages.
Bertassoni,Luiz E. et al.,"Hydrogel bioprinted microchannel networks for vascularization of tissue engineering constructs", Lab on a Chip, vol. 14, No. 13, Jan. 1, 2014, 10 pages.

* cited by examiner

DENTAL PULP CONSTRUCT

RELATED APPLICATIONS

This application is a National Stage of International Application No. PCT/US2018/035200, filed May 30, 2018, which claims priority benefit of U.S. Provisional Patent Application No. 62/512,675, filed May 30, 2017, which are hereby incorporated by reference in their entireties.

STATEMENT AS TO RIGHTS TO INVENTIONS MADE UNDER FEDERALLY SPONSORED RESEARCH AND DEVELOPMENT

This invention was made with government support under Grant No R01DE026170 and UL1 TR002369 awarded by the National Institutes of Health. The government has certain rights in the invention.

FIELD OF THE INVENTION

Provided herein are methods and processes for forming a hydrogel dental pulp replacement matrix useful in the regeneration of pulp tissue.

BACKGROUND OF THE INVENTION

Dental pulp is the innervated, unmineralized connective tissue that occupies a mineralized chamber in the center of the tooth, spanning from the root apex through the crown. The formation of dentin, the tissue surrounding the pulp, is achieved by odontoblasts, which are specialized cells that are located in a pseudo-stratified layer at the periphery of the pulp chamber. Among other tissue components, such as fibroblasts, neurons, and resident stem cells, the pulpal tissue comprises a network of blood capillaries that traverse centrally through the pulp extending towards the tooth crown. Microcapillaries branching outwards from the core vessel form a capillary-rich plexus a few micrometers away from the odontoblast layer near the dentin.

Root canal treatment is necessary in the event of deep caries or trauma when the homeostasis of the pulp tissue is lost. Current root canal treatment methods typically involve removal of infected or necrotic tissue and replacement with inert synthetic biomaterials, thus sacrificing the biological response of the tooth. Regeneration of the pulp tissue to restore tooth function, a strategy that has been named regenerative endodontics, has been proposed as an alternative to conventional root canal therapy. The biological function of the pulp is primarily regulated via the existing vasculature, and new methods for controlled regeneration of vascularized pulp will be needed for the development of successful regenerative endontic techniques. Vascularization is a process that relies on complexly orchestrated biological events, such as the morphogenesis of endothelial cells into new hollow capillaries (vasculogenesis), the recruitment of perivascular mural cells (pericytes), and the remodeling of the existing networks into a dense vascular plexus via angiogenic sprouting.

Previous studies have shed light on the regeneration of vascularized pulp by culturing endothelial and/or stem cells on flat substrates, in three-dimensional (3D) scaffold matrices, and in scaffold-less tissue constructs. For example, stem cells from exfoliated deciduous teeth (SHEDs) have been use for differentiation into endothelial cell networks in a poly-L-lactic acid scaffold in the presence of recombinant VEGF in vitro, and in untreated scaffolds in-vivo. In another instance, a commercially available hydrogel (Puramatrix™) encapsulated with dental pulp stem cells (DPSCs) and human umbilical vein endothelial cells (HUVECs) was used to determine the role of DPSCs in the angiogenic process, and partially regenerate dental pulp in root canals was implanted in the back of immunocompromised mice. However, these strategies require time intensive biological processes for a functional and interconnected vasculature to be formed. This presents a significant hurdle towards their use in clinical practices, especially for full-length root canals of mature teeth where oxygen delivery is only achieved via the root apex. New strategies that allow for controlled regeneration of vascularized pulp, including those where engineered vasculature is present at the onset of the regenerative process, are critically necessary. The present invention meets this and other needs.

BRIEF DESCRIPTION OF THE INVENTION

The requirement for immediate vascularization of engineered dental pulp poses a major hurdle towards successful implementation of pulp regeneration as an effective therapeutic strategy for root canal therapy, especially in adult teeth. Disclosed herein are pre-vascularized, cell-laden hydrogel pulp-like tissue constructs in full-length root canals for dental pulp regeneration and methods of making those. Hydrogels with tunable physical and mechanical properties are used to determine the microenvironmental conditions (e.g., microstructure, degradation, swelling, and elastic modulus) that enhance viability, spreading and proliferation of encapsulated odontoblast-like cells, and the formation of endothelial monolayers by endothelial colony forming cells. Hydrogels with higher stiffness can enhance cell viability, spreading and proliferation, as well as endothelial cell spreading and monolayer formation. Pre-vascularized, full-length, dental pulp-like tissue constructs can be made by injecting cell-laden hydrogels in root canals of extracted teeth and fabricating channels throughout the root canals. Cells seeded into the microchannels can successfully form monolayers and undergo angiogenic sprouting within days.

It is disclosed herein that an engineered vasculature that is present from the onset of the regenerative process represents an improved strategy for regeneration of vascularized dental pulp Disclosed herein are in-vitro fabricated pre-vascularized pulp-like hydrogel tissue constructs that can be used in full-length root canals.

Disclosed herein are extracellular microenvironmental conditions that enhance the viability, spreading and proliferation of odontoblast-like cells (e.g., OD21 cells) embedded in polymeric hydrogels (e.g., gelatin methacryloyl hydrogels). In certain embodiments, hydrogel physical properties can be tuned by varying polymer concentrations. These conditions promote the formation of endothelial monolayers on hydrogel substrates with endothelial colony forming cells.

Disclosed herein is endothelialized and pre-vascularized pulp-like tissue constructs in full-length root canals in-vitro.

Disclosed are methods of tooth repair that involve adding a hydrogel to a root canal. Hydrogels are polymeric materials capable of forming crosslinked three-dimensional structures. Monomers of hydrogel polymers include hydrophilic structures and therefore three-dimensional hydrogels are capable of absorbing and retaining a significant amount of water relative to their dry volume, including 2×, 3×, 5×, 8×, 10×, 20×, and more than 20× the volume of water relative to their dry volume. Examples of hydrogels are described below and the preparation and use of hydrogels are reviewed generally including in Ahmed EM, J Adv Res 6, 105-121 (2015): incorporated by reference herein. One useful hydrogel is polyhdroxyethylmethacrylate (pHEMa or PHEMA).

Also provided are compositions and techniques that utilize different hydrogel photoinitiators to control the compressive modulus of GelMA hydrogels, as well as their pore size, to enhance vascular formation.

DETAILED DESCRIPTION OF THE INVENTION

Definitions

Figure 1A:
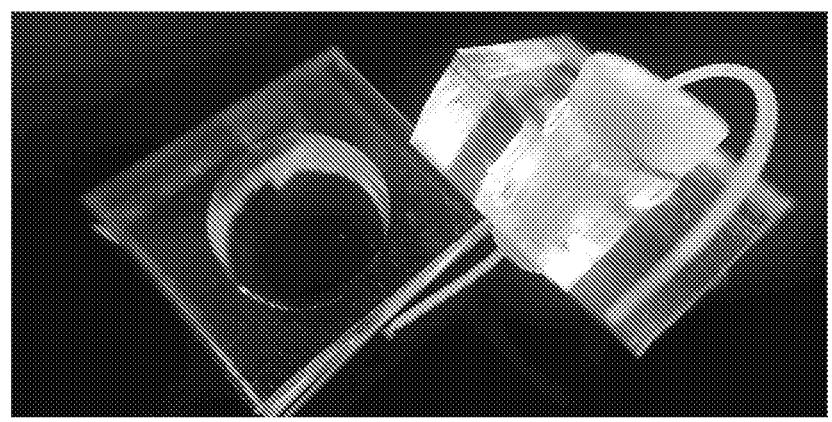
FIGS. 1A-1G provide external views of a hydrogel fabrication process in an extracted tooth fragment.
Figure 1B:
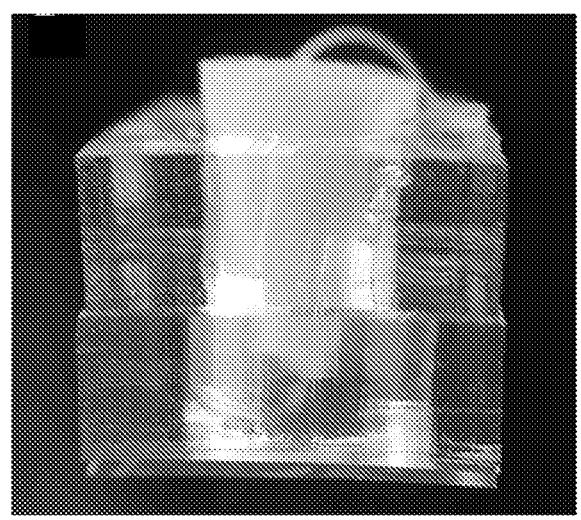
Figure 1C:
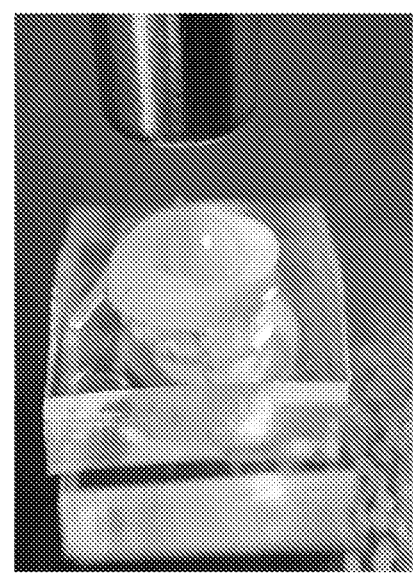
Figure 1D:
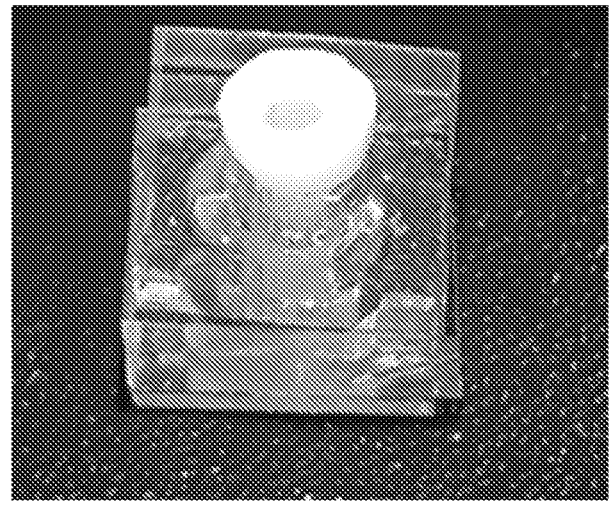
Figure 1E:
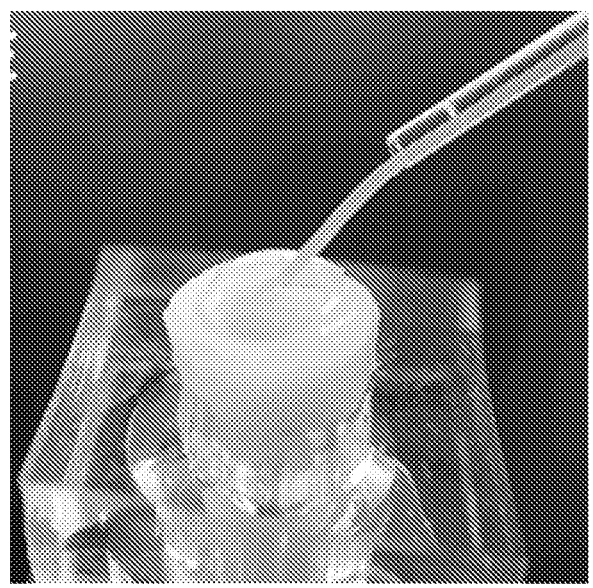
Figure 1F:
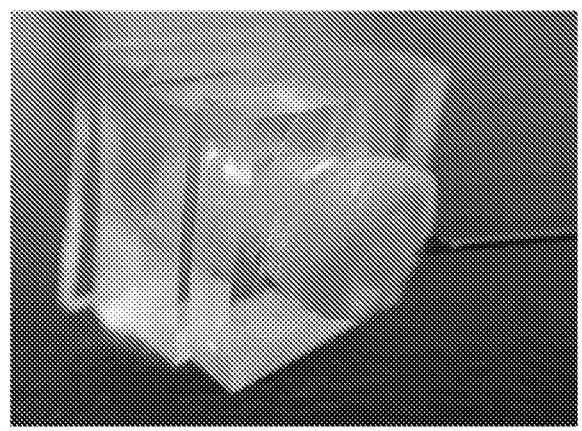
Figure 1G:
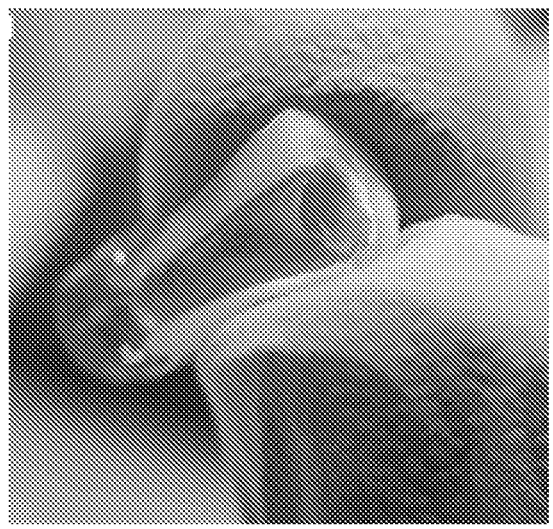

As used herein, the term "fiber" refers to a flexible, partially flexible, or rigid thread, filament, wire, tube, post, or rod capable of providing a channel of desirable dimensions in a hydrogel matrix after the hydrogel is cured and the fiber is withdrawn from the cured matrix. In a preferred embodiment, the fiber is substantially columnar or tubular in design. In another embodiment, the fiber is conical in design. In some embodiments the fiber comprises a polymer material selected from, but not limited to, polytetrafluoroethylene (PTFE, Teflon®), silicone, polyester, polyethylene (PE), poly vinyl chloride (PVC), polyurethane (PU), polypropylene (PP), polycarbonate (PC), polystyrene (PS), polyamide (nylon), acrylonitrile butadiene styrene (ABS), polybutylene terephthalate (PBT), ethylene-vinyl acetate (EVA), polyetheretherketone (PEEK), polysulfone (PSU), polyphenylsulfone (PPSF or PPSU), and polyoxymethylene (POM), or blends thereof. In one embodiment the fiber is a hydrogel fiber. In another embodiment, the fiber is a metal fiber.

In some embodiments the fiber has a diameter of from about 100 μm to about 1 mm. In other embodiments the fiber has a diameter of from about 200 μm to about 900 μm. In other embodiments the fiber has a diameter of from about 300 μm to about 800 μm. In additional embodiments the fiber has a diameter of from about 400 μm to about 700 μm. In still other embodiments the fiber has a diameter of from about 400 μm to about 600 μm. In other embodiments the fiber has a diameter of from about 450 μm to about 550 μm. In other embodiments the fiber has a diameter of from about 475 μm to about 525 μm. In other embodiments the fiber is about 500 μm in diameter.

Provided is a method of enhancing neo-vascularization in a root canal of a tooth from which natural pulp has been removed, the method comprising the steps of:
 a) positioning a fiber in the root canal of the tooth;
 b) filling at least a portion of the root canal with an unset hydrogel composition, such that the unset hydrogel composition contacts at least a portion of the fiber;
 c) setting the hydrogel composition, thereby forming a set hydrogel; and
 d) removing the fiber from the set hydrogel, thereby leaving a channel in the set hydrogel.

Also provided is a method of enhancing regeneration of vascularized dental pulp in a root canal of a tooth from which natural pulp has been removed, the method comprising the steps of:
 a) positioning a fiber in the root canal of the tooth;
 b) filling at least a portion of the root canal with an unset hydrogel composition, such that the unset hydrogel composition contacts at least a portion of the fiber;
 c) setting the hydrogel composition, thereby forming a set hydrogel; and
 d) removing the fiber from the set hydrogel, thereby leaving a channel in the set hydrogel.

Further provided is a method of promoting formation of endothelial monolayers on a set hydrogel in a root canal of a tooth from which natural pulp has been removed, the method comprising the steps of:
 a) positioning a fiber in the root canal of the tooth;
 b) filling at least a portion of the root canal with an unset hydrogel composition, such that the unset hydrogel composition contacts at least a portion of the fiber;

c) setting the hydrogel composition, thereby forming the set hydrogel; and d) removing the fiber from the set hydrogel, thereby leaving a channel in the set hydrogel.

One embodiment for each method described herein comprises using an unset hydrogel composition comprising a gelatin methacroyl hydrogel. In another embodiment the unset hydrogel composition comprises gelatin methacroyl at a concentration of at least about 10% (w/v). In another embodiment the unset hydrogel composition comprises gelatin methacroyl at a concentration of at least about 15% (w/v).

A root canal procedure involves drilling an opening into an affected tooth that has a root canal that is infected or has substantial decay such that the root canal is damaged. An opening (2-4 mm wide) is formed in the top of the tooth, the infected or inflamed tissue is removed from the root canal (often with an endodontic file and irrigation). The root canals are then filled with a material that prevents further infection.

As disclosed herein, the material used to fill the root canal is a hydrogel, e.g., a hydrogel comprising gelatin methacroyl. The gelatin methacroyl can be at least 5% (w/v) of the unset hydrogel composition, at least 8% (w/v) of the unset hydrogel composition, at least 10% (w/v) of the unset hydrogel composition, at least 12% (w/v) of the unset hydrogel composition, at least 14% (w/v) of the unset hydrogel composition, at least 15% (w/v) of the unset hydrogel composition, at least 20% (w/v) of the unset hydrogel composition, or higher. In some embodiments, the hydrogel is pre-loaded with cells, e.g., cells from a subject (including, but not limited to, a human subject) undergoing the procedure. Such cells include odontoblasts, endothelial colony forming cells or multipotent or pluripotent stem cells. In other embodiments, cells from the subject migrate into the hydrogel after the root canal is filled and the hydrogel is set.

The disclosed method can be used with a variety of different hydrogels, such as polyethylene glycol diacrylate (PEGDA), polyethylene glycol dimethacryalte (PEGDMA), and star poly(ethylene glycol-co-lactide) acrylate (SPELA), as well as non-photo-crosslinkable materials, such as collagen. Moreover, the fact that the proposed photo-crosslinkable material can also be photocured (i.e., set) using a conventional dental curing light makes this strategy more readily translatable from a clinical standpoint.

The methods further include inserting one or multiple fiber(s) into the hydrogel. The fiber(s) is configured to create one or multiple channel(s) through the hydrogel after being removed from the hydrogel. The fiber can be of any appropriate material including, but not limited to, a pre-solidified hydrogel. Examples of pre-solidified hydrogels include, agarose hydrogels, alginate hydrogels, pluronic F127 hydrogels, and the like. In some embodiments, the hydrogel fiber comprises 3-9% (w/v) agarose, or 4-8% (w/v) agarose, or 5-7% (w/v) agarose, or 5.5-6.5% (w/v) agarose, or 5.9-6.1% (w/v) agarose, or any subrange of such agarose concentrations. Hydrogel fibers containing<3% (w/v) agarose were found to be too brittle for procedural use while agarose mixtures>10% (w/v) proved too viscous during fiber formation procedures. In some embodiments, the hydrogel fiber comprises 1-6% (w/v) alginate, or 2-5% (w/v) alginate, or 3-4% (w/v) alginate, or 3.5-4.5% (w/v) alginate, or any subrange of such alginate concentrations. Hydrogel fibers containing<1% (w/v) alginate produce fibers that do not have adequate structural integrity for aspiration procedures. Alginate hydrogels fibers containing>6% (w/v) alginate are subject to high degrees of water absorption, resulting in hydrogel swelling and inaccurate fiber dimensions. In some embodiments, the hydrogel fiber comprises 20-40% (w/v) pluronic F127, or any subrange of such pluronic F127 concentrations.

The fiber is typically placed at or near the center of the hydrogel, e.g., within 500 μm of the center, or within 400 μm of the center, or within 300 μm of the center, or within 200 μm of the center, or within 100 μm of the center, or within 50 μm of the center, or within 20 μm of the center, or closer than 20 μm from the center of the hydrogel.

Also provided is a kit comprising: an unset hydrogel in a first container; a fiber in a second container; and instructions for use of the unset hydrogel and the fiber in filling the root canal of a tooth. In some embodiments, the unset hydrogel composition in the kit comprises a crosslinkable polymer. In some embodiments, the unset hydrogel composition comprises gelatin methacroyl. In further embodiments the unset hydrogel composition comprises at least about 10% (w/v) gelatin methacroyl. In other embodiments hydrogel composition comprises at least about 15% (w/v) gelatin methacroyl. In other embodiments hydrogel composition comprises at least about 20% (w/v) gelatin methacroyl. In some embodiments, the compositions herein, including those in the kits herein, include a photoinitiating agent in the unset hydrogel composition. In some embodiments the unset hydrogel composition also comprises a photoinitiator, such as 0.01%-1.5% (w/v) lithium phenyl-2,4,6-trimethylbenzoyl phosphinate. In other embodiments, the photoinitiator is from about 0.025 to about 0.1% (w/v) lithium acylphosphinate (LAP). In other embodiments, the photoinitiator is from about 0.04 to about 0.08% (w/v) lithium acylphosphinate (LAP). In other embodiments, the photoinitiator is from about 0.05 to about 0.075% (w/v) lithium acylphosphinate (LAP). In some embodiments, the unset hydrogel and a photoinitiator are in a saline solution, preferably a buffered saline solution, such as Dulbecco's phosphate buffered saline.

One embodiment provided is a kit comprising:

a) an unset gelatin methacroyl hydrogel and a lithium acylphosphinate photoinitiator in a first container;

b) a fiber in a second container; and c) instructions for use of the unset hydrogel, photoinitiator, and the fiber in filling the root canal of a tooth.

Another embodiment provides a kit comprising:

a) an unset gelatin methacroyl hydrogel and from about 0.04% to about 0.08% (w/v) of a lithium acylphosphinate photoinitiator in a first container;

b) a fiber in a second container; and c) instructions for use of the unset hydrogel, the photoinitiator, and the fiber in filling the root canal of a tooth.

Another embodiment provides a kit comprising:

a) an unset gelatin methacroyl hydrogel comprising from about 5% to about 25% gelatin methacroyl prepolymer, a buffered saline, and from about 0.04% to about 0.08% (w/v) of a lithium acylphosphinate photoinitiator in a first container;

b) a fiber in a second container; and c) instructions for use of the unset hydrogel, the photoinitiator, and the fiber in filling the root canal of a tooth.

The methods further involve setting the hydrogel (e.g., photo-crosslinking the hydrogel using a light source). Photopolymers are polymers that exhibit a change in properties when exposed to light such as visible or ultraviolet (UV) or visible light. Some photopolymers, including methacroyl gelatin will crosslink upon exposure to ultraviolet light. In embodiments, a first volume of hydrogel is added to the root canal, where the first volume fills the first 2.5-3.5 mm of the root canal. This first volume is then crosslinked using a UV light. A second volume of the hydrogel is then added to the root canal and fills the next 2.5-3.5 mm of the root canal. This second volume is then crosslinked using the UV light. Then a third volume of the hydrogel is added to the root canal and fills the remainder of the root canal. This third volume is crosslinked using the UV light. In order to provide sufficient UV light to cure the hydrogel but not enough to kill cells in the tooth root, the illumination time and light source power can be varied. For example, a 155 mW light source can be used for 30 seconds to crosslink the hydrogel. However, hydrogels may be exposed for different crosslinking times or a range of light intensities, depending on the depth of the hydrogel in the root canal. As a non-limiting example, an 800 mW UV light source may be placed at a distance of about 13-19 mm from an affected tooth to cure a first volume of hydrogel, at a distance of about 40-46 mm from the affected tooth to cure a second volume of hydrogel, and at a distance of about 80-90 mm from the affected tooth to cure the third volume of hydrogel.

The following examples are for illustration only. In light of this disclosure, those of skill in the art will recognize that variations of these examples and other examples of the disclosed invention be possible without undue experimentation.

Example 1—Gelatin Methacrylolyl (GelMA) Synthesis

GelMA was synthesized following previously published protocols. Briefly, 10% (w/v) type A gelatin from porcine skin (Sigma) was dissolved in Dulbecco's phosphate buffered saline (DPBS, Sigma). The solution was stirred and heated to 50° C. and 8% (v/v) methacrylic anhydride (Sigma) was added to the solution in a dropwise manner. The reaction was allowed to proceed for 2 hours at 50° C. before being stopped using a 5×dilution of 40° C. DPBS. The resulting solutions were dialyzed against distilled water using 12-14 kDa dialysis tubing at 45±5° C. for five days with two water changes per day. The solution was then stored at −80° C. overnight and lyophilized for 5 days prior to use.

Example 2—Hydrogel Preparation

GelMA macromer at concentrations of 5, 10 and 15% (w/v) was dissolved in DPBS with 0.01%-1% (w/v) Lithium Phenyl (2,4,6-trimethyl-benzoyl) phosphinate (Tokyo Chemical Industries) photoinitiator (also referred to as lithium phenyl-2,4,6-trimethylbenzoylphosphinate). GelMA hydrogels were fabricated by dispensing the hydrogel precursors and exposing samples to blue light (405±5 nm) (VALO Cordless) with a power of 1650 mW for 5 seconds at a distance<1 cm.

Example 3—Physical and Mechanical Characterization

Hydrogel pore structure and morphology was analyzed via scanning electron microscopy. To that end, 5, 10 and 15% (w/v) GelMA hydrogel disks (n=3) were prepared as described above, cross-sectioned, flash frozen in liquid nitrogen and lyophilized overnight. Samples were then coated with gold/palladium and imaged using a FEI Quanta 200 SEM at 20.0 kV. For swelling analyses, 5, 10 and 15% (w/v) GelMA hydrogel discs (n=6) were stored for 24 hours at room temperature in DPBS, removed from the solution, blot dried, and the swollen weight recorded. The dry weights of the samples was collected after sample lyophilization and the mass swelling ratio was calculated as the ratio of the wet mass to the dry mass of the polymer. Hydrogel degradation was determined by incubating GelMA hydrogel disks (n=6) for 5, 12 and 24 hours at 37° C. in a 2.5 U ml-1 collagenase solution (MP Biomedical). After incubation, the non-degraded hydrogel fragments were retrieved and the solution removed. Samples were then rinsed with DPBS before removal of excess liquid and lyophilization overnight. Degradation percentage was determined by calculating the weight ratio of degraded versus intact hydrogel samples at each time point. Lastly, hydrogel elastic modulus was tested in unconfined compression at a loading rate of 1 mm/minute on a universal mechanical testing machine (Instron 5542). Prior to testing 5, 10 and 15% (w/v) GelMA hydrogel disks (n=6) were stored in DPBS for 24 h. Samples were then blot dried and the elastic modulus of the hydrogel was determined as the slope of the linear region corresponding to 0%-10% strain.

An odontoblast-like cell line (OD21) was used to determine the behavior of odontoblast-like cells in the engineered hydrogels. OD21 cells were cultured in DMEM containing 10% (v/v) fetal bovine serum (FBS) and 1% (v/v) penicillin-streptomycin. Primary baboon endothelial colony forming cells (ECFC)—isolated from peripheral blood were used to study endothelial monolayer formation. ECFCs from passage 5-6 were cultured in endothelial cell growth medium (EGM-2 MV, Lonza), also containing 10% (v/v) fetal bovine serum (FBS) and 1% (v/v) penicillin-streptomycin. All cells were maintained in a humidified, 37° C., 5% $CO_2$ incubator, and the media changed every two days with two cells passages per week for OD21 and once per week for ECFC.

Example 5—OD21 Cell Encapsulation, Viability, Proliferation, and Spreading

Cell-laden hydrogel constructs were fabricated by dispensing 5 µl of a cell-laden GelMA hydrogel precursor ($5 \times 10^6$ cells $ml^{-1}$) on TMSPMA coated glass slides. The hydrogel precursor was then compressed to 100 µm thick disks and photocrosslinked as described above. The viability of OD21 in 5, 10 and 15% (w/v) GelMA hydrogels was observed using a membrane permeability live/dead assay kit (Molecular Probes). The live and dead cells were counted using ImageJ software using at least 3 locations of triplicate samples after 1, 4, and 7 days. The percentage of viable cells was then calculated based on the number of live cells divided by the total cell number. Cell proliferation was determined using an ActinGreen/NucBlue assay kit (Molecular probes), for which the constructs were first fixed in 4% (v/v) paraformaldehyde (Electron Sciences) for 30 min, permeabilized in 0.1% (w/v) Triton X-100 solution for 20 min and blocked in 1% (w/v) bovine serum albumin (BSA) for 1 h. Samples were then incubated in the ActinGreen staining solution for 45 min at room temperature, and in a NucBlue staining solution for 10 min at 37° C. to stain the cell nuclei. Samples were imaged using either an inverted fluorescence microscope (FL Auto, Evos) or a laser scanning confocal microscope (ZEISS Airyscan LSM 880). The number of cells in each sample was computed using ImageJ software in three samples per group after 1, 4 and 7 days.

Example 6—ECFCs, Spreading and Monolayer Formation

To study the formation of endothelial monolayers on GelMA hydrogels of different physical and mechanical properties, ECFCs (1×10⁴ cells ml⁻¹) were seeded on top of pre-molded hydrogels of 5, 10 and 15% (w/v) concentrations. Endothelial cell coverage was calculated by counting the number of cells per mm2 on ImageJ. Cell spreading was qualitatively evaluated using an ActinGreen/NucBlue assay kit as described above.

Example 7—Fabrication of Pre-Vascularized Dental Pulp-Like Tissue Constructs Freshly extracted human pre-molars (n=3) were sectioned into 9 mm long root fragments having approximately 1.5 mm apical foramen diameter. Root fragments were UV sterilized (800±10 mW, 10 min) and immersed in a 1% (v/v) penicillin-streptomycin solution for 24 h. Root canals in the tooth fragments were then prepared into a conical shape and sectioned longitudinally to allow for easier retrieval of the hydrogel samples after tissue culture. After sectioning, the two root halves were re-attached and secured by wrapping them with using laboratory film (Parafilm M). The root fragments were irrigated with 5 ml of 17% (w/v) EDTA to expose the bioactive molecules sequestered within the dentin. To fabricate the microchannels, 500 μm diameter 6% (w/v) agarose fibers were prepared using a glass capillary fitted with a metallic piston inside. The pre-solidified agarose fibers were manually positioned inside of the tooth, and the laboratory film was used to support the fibers in approximate center of the tooth. Based on the observation that 15% GelMA hydrogels lead to advantageous spreading of OD-21 and monolayer formation of ECFC cells, the 15% GelMA hydrogel precursor was chosen for proof-of-principle fabrication of the pre-vascularized dental pulp model. OD-21 cell-laden hydrogel precursor was injected into the pulp chamber/root canal to fully surround the agarose fiber. The tooth fragment was filled 3 mm at a time to ensure homogenous photopolymerization of the hydrogel precursor. The detailed fabrication process is described in FIGS. 1A-1G. After photopolymerization of the GelMA hydrogel, the agarose fiber was aspirated from the hydrogel using a light vacuum, as previously described. ECFCs were then seeded into the fabricated microchannels, while the construct was oriented horizontally in 4 separate seeding events (1×10⁶ cells ml⁻¹ per seeding) with 1 hour between seedings to allow for cell attachment. Tissue constructs were then cultured in a combined DMEM and EGM-2 MV medium at a proportion of 1:1. After 7 days of culture, hydrogel samples were retrieved from the tooth, stained with ActinGreen/NucBlue, and immunostained for CD31. Briefly, the samples were fixed in 4% paraformaldehyde for 20 min and permeabilized in 0.1% (v/v) Triton X-100 for 30 minutes. Samples were then blocked with 1.5% (w/v) bovine serum albumin for 1 hour at room temperature and exposed to a 1/50 dilution of mouse monoclonal antibodies against CD31 (Dako). The gels were washed in DPBS three times before the addition of a 1/250 dilution of the secondary antibody, conjugated goat anti-mouse (Thermo Scientific) and allowed to incubate at room temperature for 2 hours followed by copious rinsing with DPBS prior to imaging using a confocal laser scanning microscope.

Example 8—Statistics

Statistical analysis was performed using GraphPad Prism 6 for sections 4.1-4.3. The values represent averages±standard deviations. One-way/two-way ANOVA was used to analyze the differences between GelMA concentrations and culture time followed by Tukey post-hoc tests ($\alpha=0.05$).

Example 9—Pre-Vascularized Full-Length Dental Pulp-Like Tissue Constructs

Disclosed are pre-vascularized dental pulp-like cell-laden tissue constructs in full-length root canals and an in-vitro method to fabricate them. Also disclosed are the physical and mechanical properties of photo-crosslinkable GelMA hydrogel scaffolds that enhance OD21 and ECFC viability and function. GelMA hydrogels have been extensively utilized for a variety of tissue engineering applications, however such scaffold materials have not been used in dental pulp regeneration.

Example 10—Microstructure and Physical Properties of GelMA Hydrogels

Figure 2A:
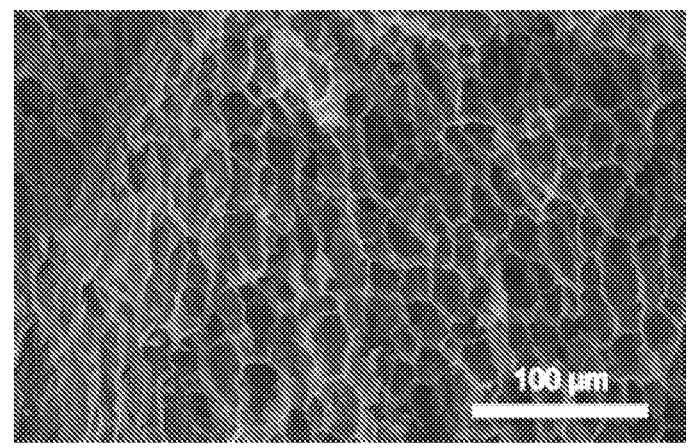
FIGS. 2A-2C provide 100 μm SEM views of cross-sectioned GelMA hydrogels of 3 w/v concentrations.
Figure 2B:
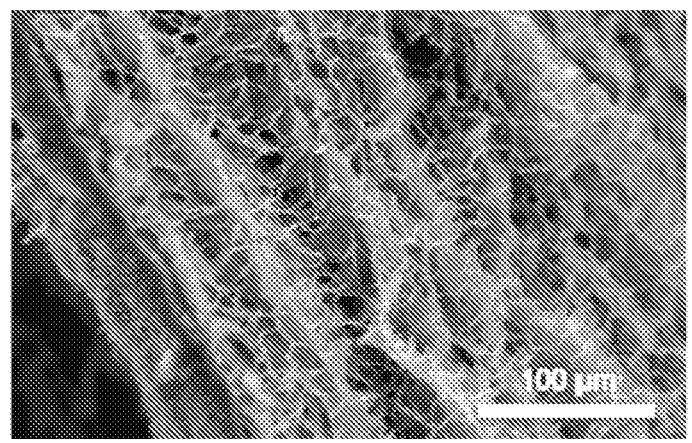
Figure 2C:
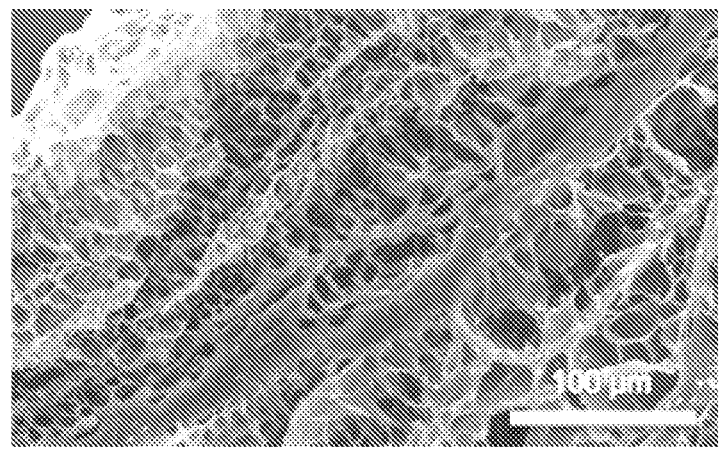
Figure 3:
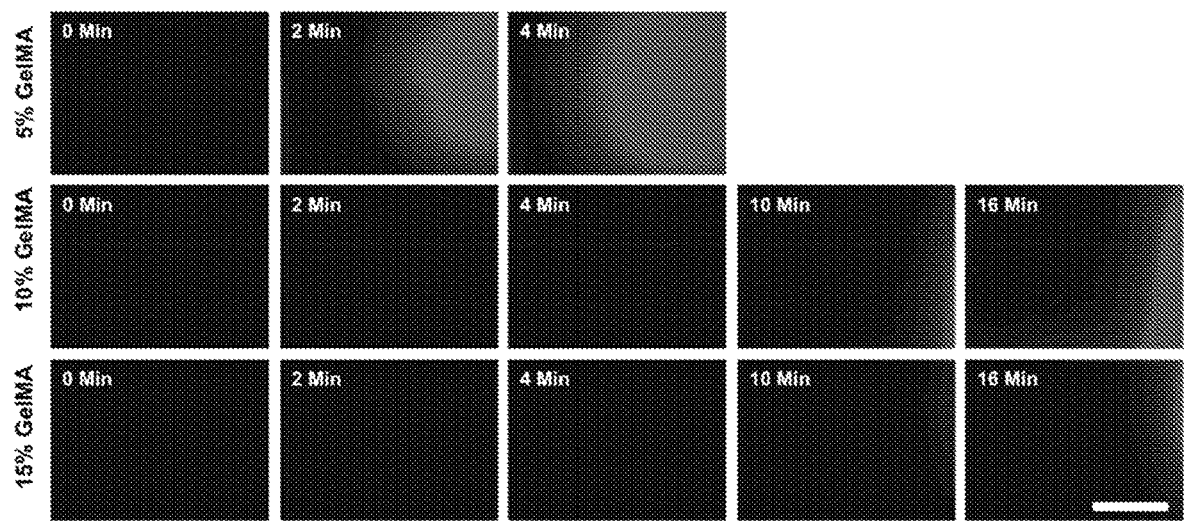
FIG. 3 represents comparative rates of rhodamine dye solution diffusion through tested hydrogels.
Figure 4A:
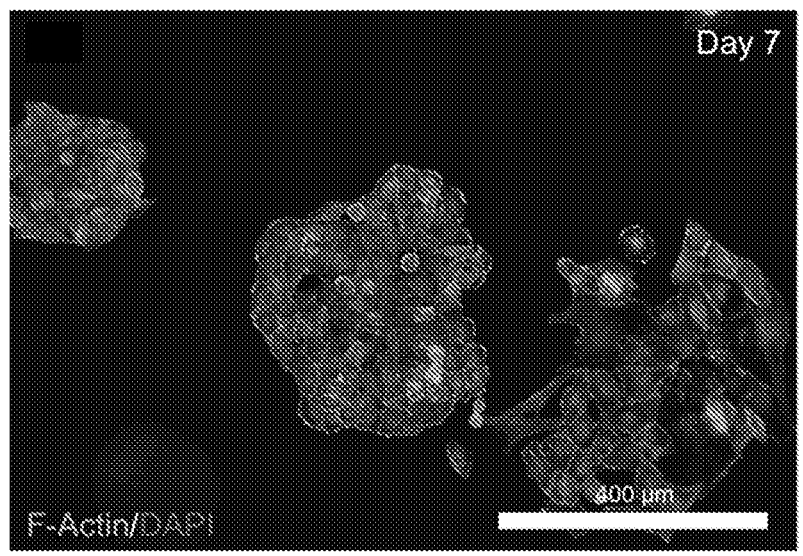
FIGS. 4A-4C provide micrographs of cells proliferated in tested hydrogels over 7 days.
Figure 4B:
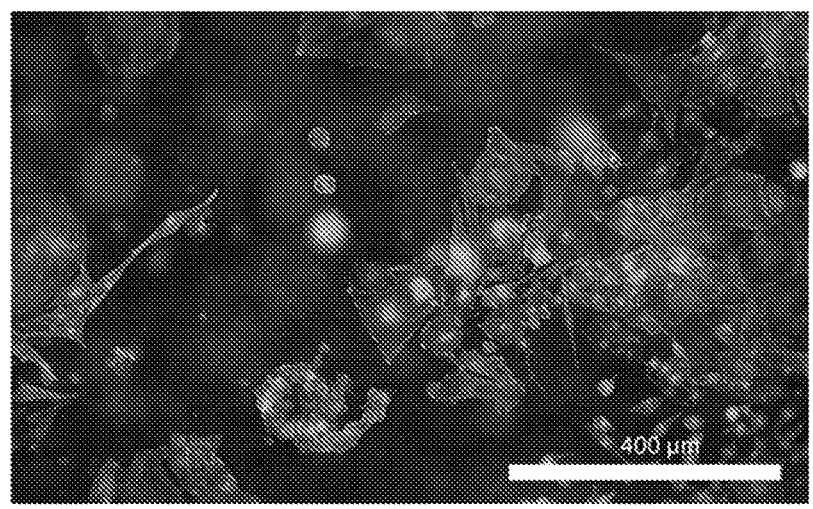
Figure 4C:
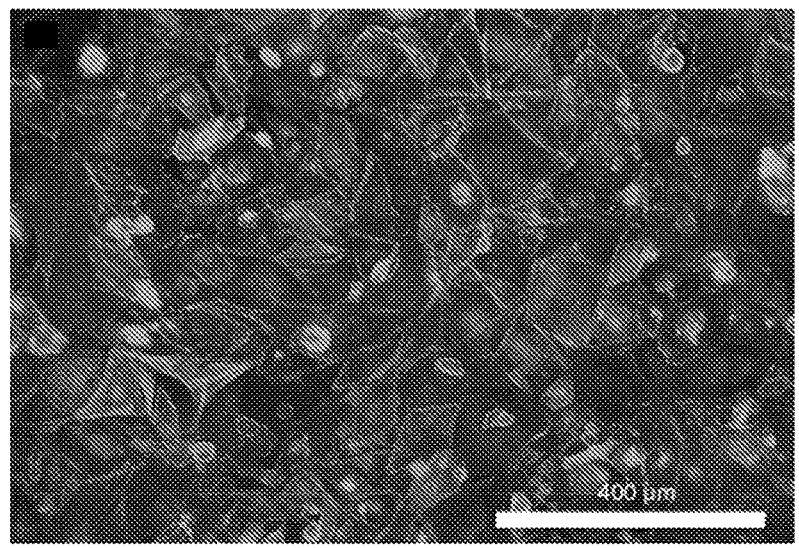
Figure 4D:
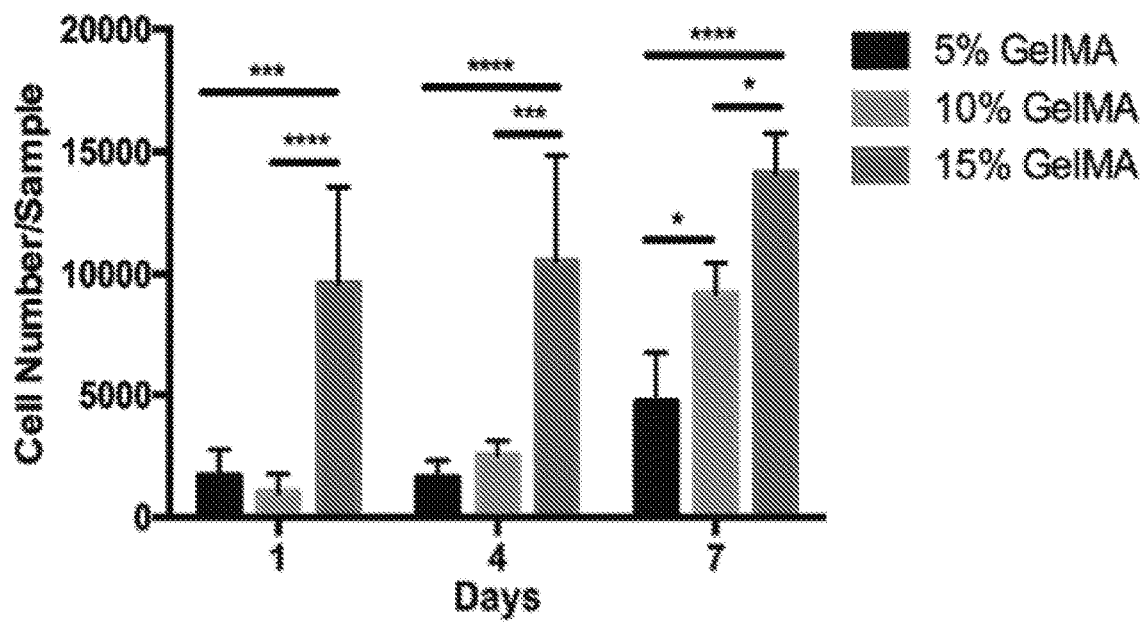
FIG. 4D represents cell numbers determined for tested hydrogels after 7 days.
Figure 5A:
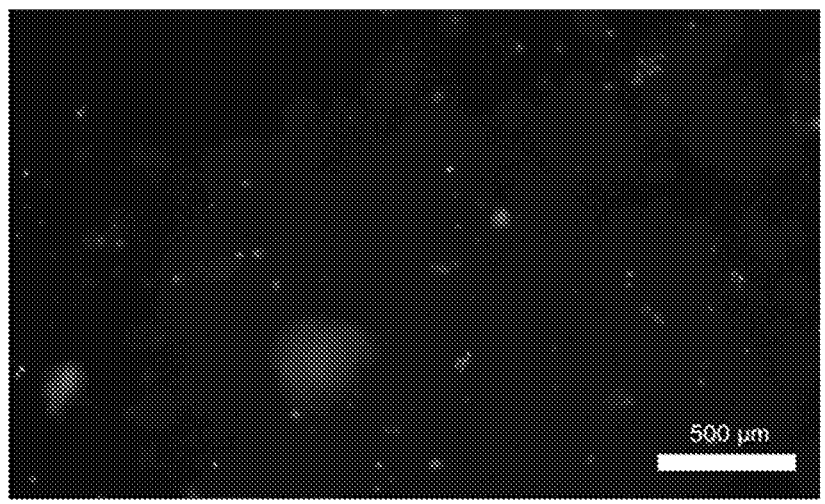
FIGS. 5A-5C are micrographs of OD21 cells in tested hydrogels after 7 days.
Figure 5B:
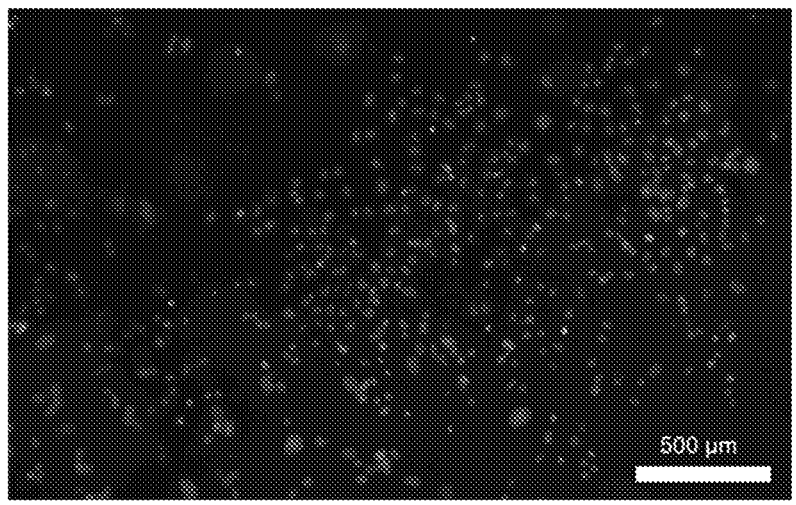
Figure 5C:
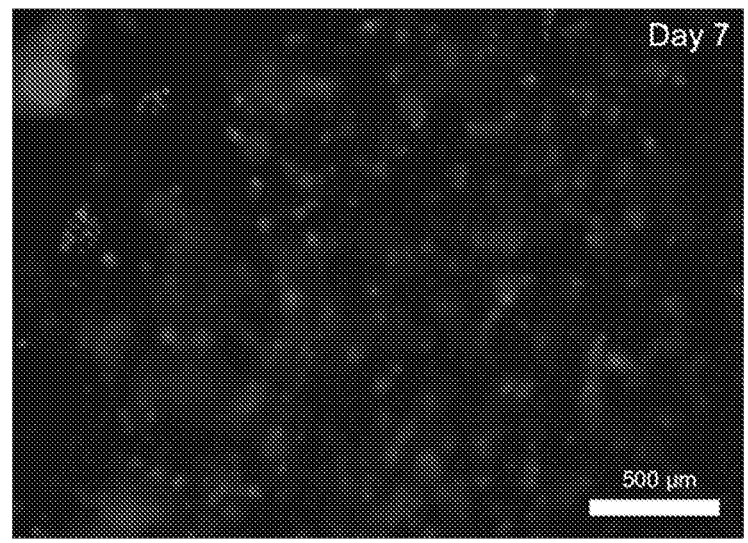
Figure 5D:
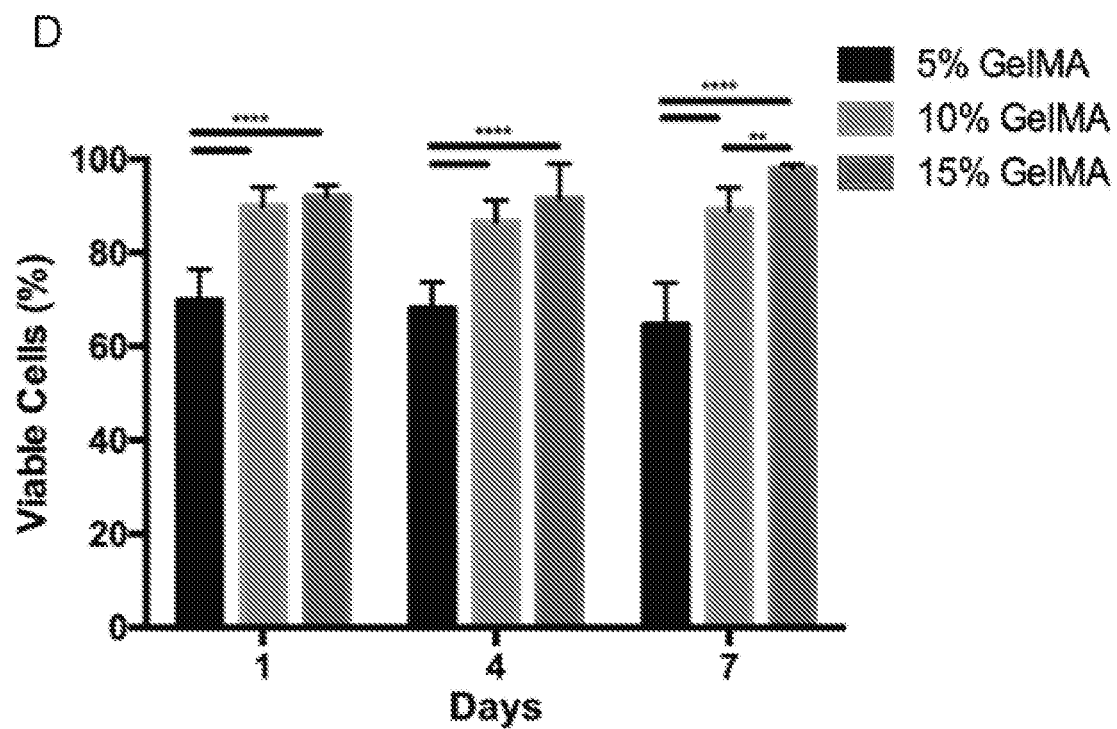
FIG. 5D represents the viable OD21 cell numbers in the tested hydrogels after 7 days.

The physical properties of hydrogels such as porosity, degradability, swelling and mechanical properties are influenced by the nature and extent of crosslinking of the polymer during gelation, and are known to affect cell behavior and function during tissue formation. SEM analysis (FIGS. 2A-2C) of cross-sectioned GelMA hydrogels of 5%, 10% and 15% (w/v) concentrations showed a honeycomb-like structure in all three groups. Both 10% and 15% hydrogel groups appeared to have smaller pore sizes (FIGS. 2B-2C) than 5% (FIG. 2A) GelMA, thus indicating the formation of denser crosslinked networks in hydrogels with higher concentrations. The rate of diffusion of a rhodamine dye solution through each of these hydrogels corresponded with their apparent pore sizes (FIG. 3), where 5% GelMA hydrogels were visibly more permeable. Also, the increased polymer volume fraction correlated with increased thickness of the pore walls. However, the pore sizes of 10% and 15% GelMA hydrogels were not noticeably different from one another.

Figure 2D:
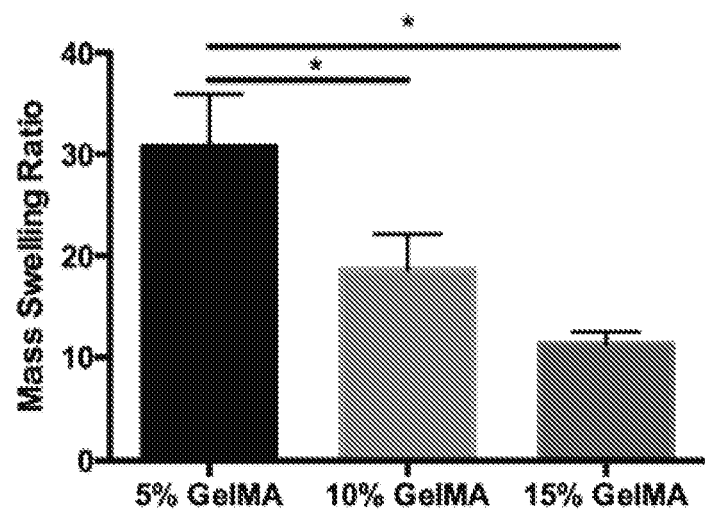
FIG. 2D depicts mass swelling ratios observed for tested hydrogels.
Figure 2E:
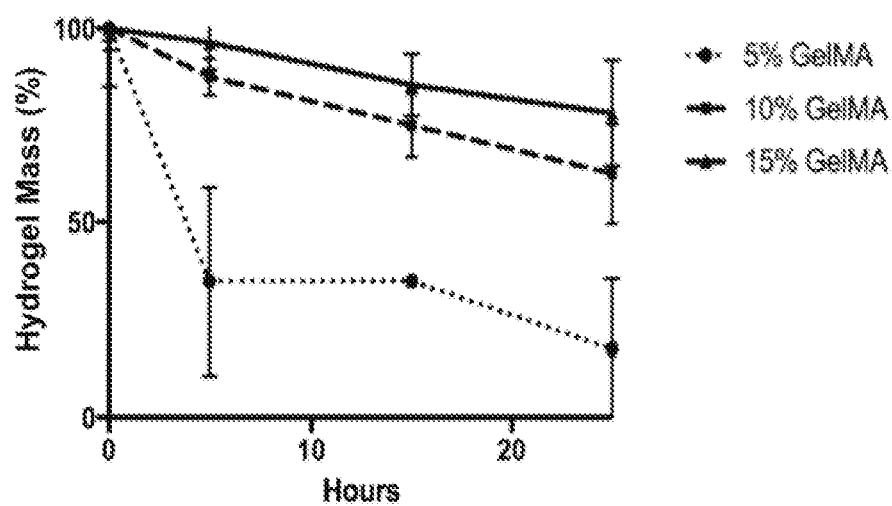
FIG. 2E depicts mass degradation by collagenase of tested hydrogels.

Transport of biological molecules in microporous hydrogels occurs almost solely through diffusion of solutes, thus the capacity of a hydrogel to swell is indicative of the diffusivity of fluids through the scaffold. 5% GelMA hydrogels had significantly higher mass swelling ratios (FIG. 2D) which were nearly two- and three-fold higher than those of 10% and 15% GelMA hydrogels, respectively, which is consistent with the pore size structure seen in SEM images. 5% GelMA hydrogels were also more susceptible to degradation by collagenase (FIG. 2E) and underwent 83% degradation within a 24-hour period, while 10% and 15% GelMA hydrogels were degraded to an extent of only 38% and 22%, respectively. Cell-mediated degradation of hydrogels has been shown to influence stem cell differentiation through cell spreading and cellular traction, with higher degradability prompting osteogenic phenotypes in human Mesenchymal Stem Cells (hMSCs). OD21 cells encapsulated in 10% and 15% GelMA hydrogels were more spread than those in 5% GelMA hydrogels (FIG. 4), suggesting a closer correlation between cell spreading and hydrogel elasticity than cell spreading and hydrogel degradation.

Figure 2F:
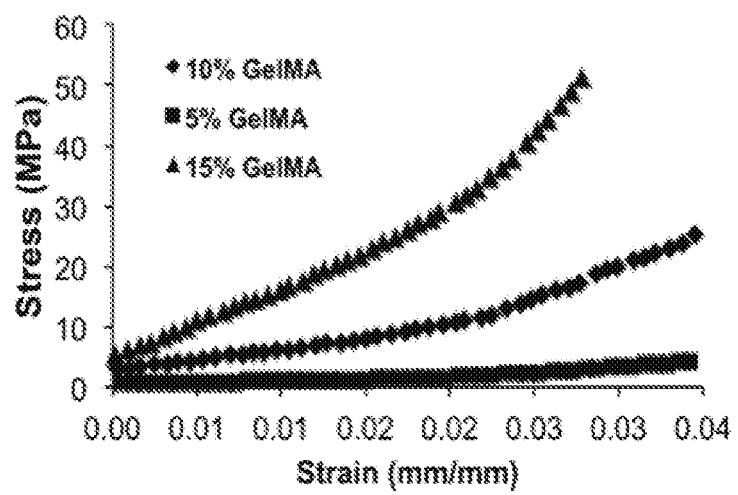
FIG. 2F represents stress-strain curves calculated for tested hydrogels.
Figure 2G:
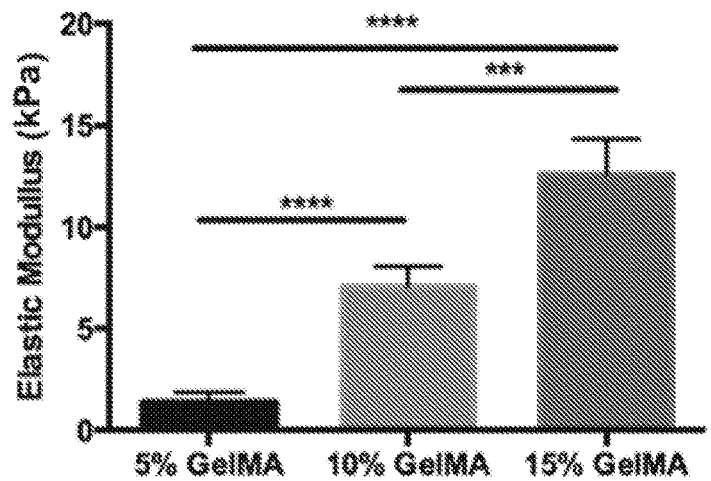
FIG. 2G represents elastic moduli determined for tested hydrogels.

Unconfined compression of the 5, 10 and 15% hydrogels revealed a steeper stress-strain curve (FIG. 2F) and a correspondingly higher elastic modulus (FIG. 2G) for the higher concentration gels (12 kPa) in comparison to the 10% (7 kPa) and 5% (1.5 kPa) gels. Given the higher polymer concentration, 15% GelMA hydrogels were also more densely cross-linked, which appeared to have a more profound effect on the elasticity of the hydrogels than degradation, porosity or swelling, which were comparable between 10 and 15%.

Example 11—OD21 Cell Viability, Spreading and Proliferation in GelMA Hydrogels

Matrix mechanical properties play a significant role in cell behavior and function. The mechanical forces exerted by the extracellular microenvironment are relayed through integrin-mediated adhesions to the nucleus, thus activating a host of signaling pathways that modulate cell survival, proliferation and differentiation. Early cell response to these forces is manifested in the form of cell spreading where cells undergo cytoskeletal remodeling to match the tension exerted by the matrix and therefore stiffer matrices induce increased cell spreading in contractile cells. Cell morphology is strongly linked to cell cycle progression and cell lineage commitment through the RhoA-ROCK pathway and studies have shown that matrices that promoted cell spreading induced osteogenesis (stiffer tissue lineages) in hMSCs, while those that restricted cell spreading directed them towards adipogenic (softer tissue lineages) phenotypes. Also, other studies have ascertained that stem cell lineage specification can be directed by matrix elasticity by mimicking the elastic properties of the desired native tissue. While these conclusions are valid for 2D cultures on hydrogels, the above effects are further exaggerated for cells encapsulated in 3D scaffolds. These effects have not previously been examined on the OD21 cell line used in the studies described herein.

OD21 cells encapsulated in 5, 10 and 15% GelMA hydrogels showed higher survival rates in the stiffer gels even at early time points and the effect was sustained through the 7 day period of the study (FIGS. 5A-5D). At later time points, cells displayed a statistically significant preference for 15% over the 10% GelMA hydrogels. The cells in the stiffer (15%) gels were more spread which translated to a three times higher rate of proliferation over a 7 day period than that in softer gels (5%) (FIGS. 4A-4D). The cells closest to the substrate support in the cell-laden hydrogels were more spread, which further suggests the propensity of this cell line for higher spreading near stiffer matrices or substrates. This is in keeping with what is known about cell responses to matrix elasticity, since the OD21 cells appeared to thrive in stiffer matrices like the lightly calcified pre-dentin at the periphery of the dental pulp, the site of these cells in native tissues.

Example 12—Effect of GelMA Hydrogel Elasticity on Monolayer Formation by ECFCs

Figure 6A:
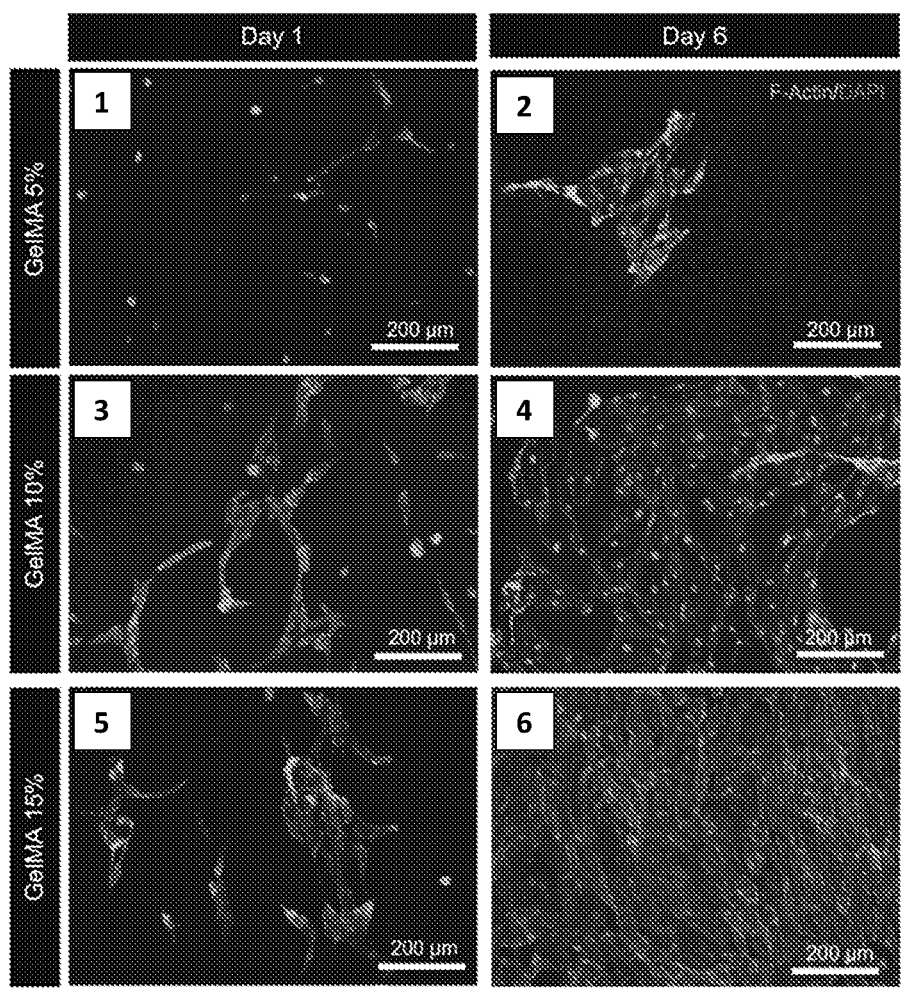
FIG. 6A depicts ECFCs cultured in flat substrates on days 1 and 6.
Figure 6B:
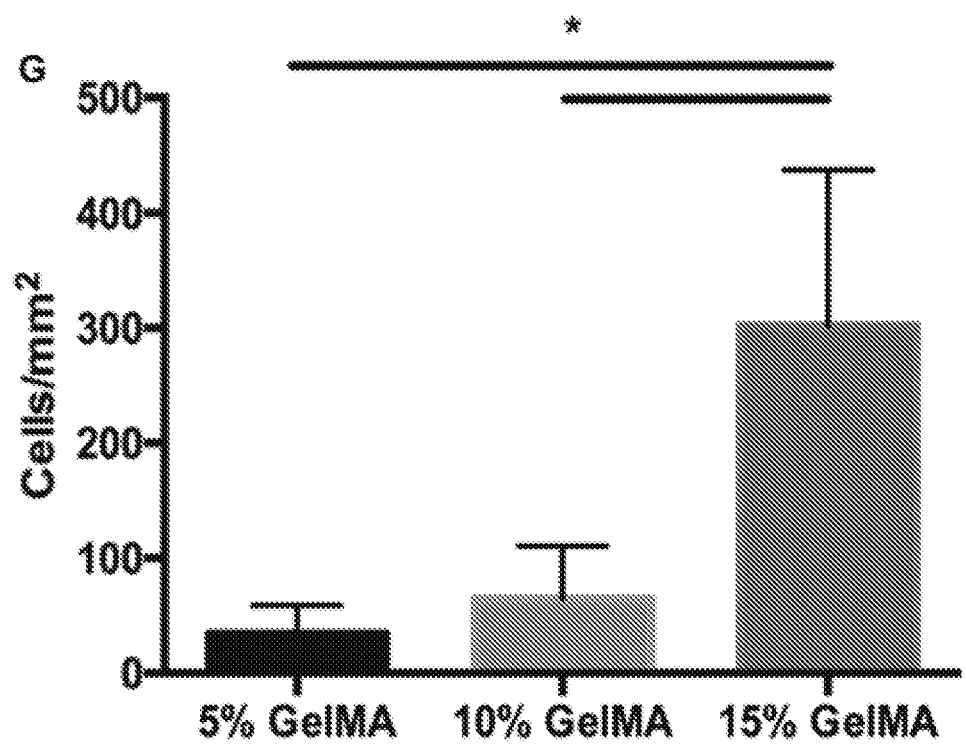
FIG. 6B represents the relative ECFC cell numbers in flat substrates on days 1 and 6.
Figure 7A:
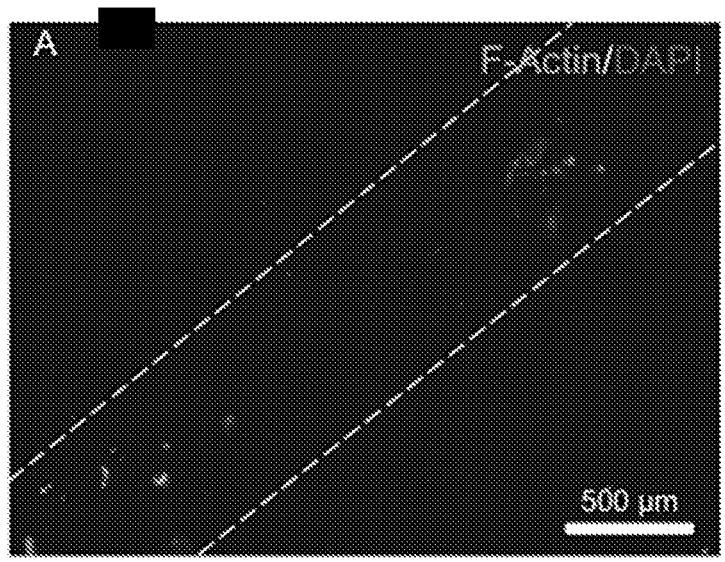
FIGS. 7A-7C depict ECFCs cultured in tested hydrogel microchannels.
Figure 7B:
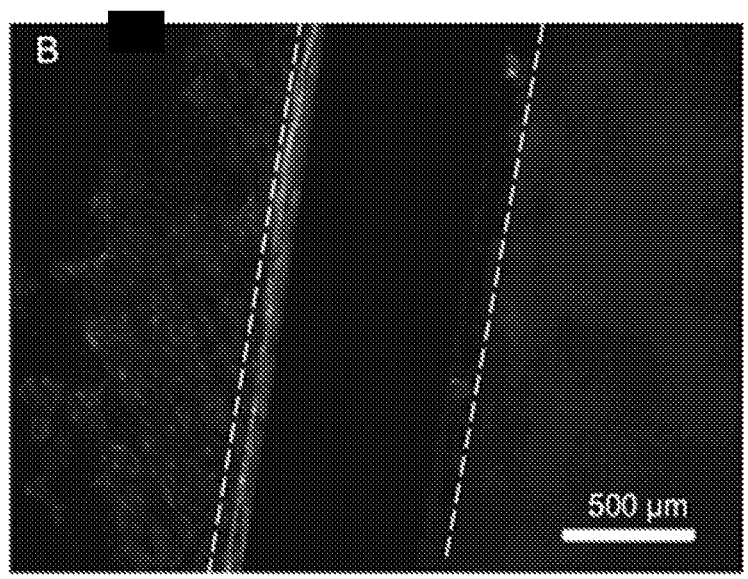
Figure 7C:
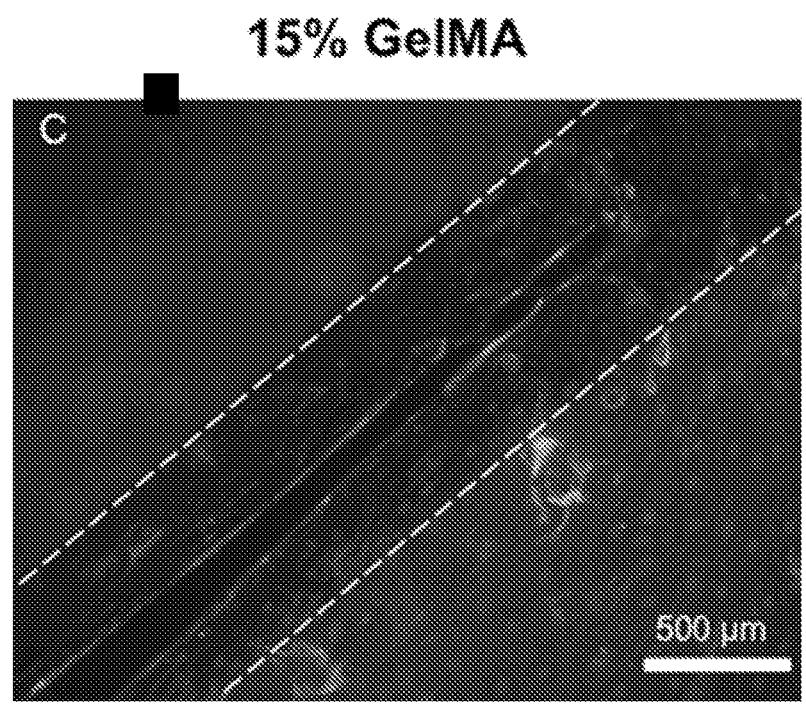

Vascular cell behavior is modulated by the mechanical properties exerted by the arterial membrane. The endothelial cells forming the blood vessels are in contact with and influenced by the tensile forces exerted by the basal and outer membranes of the arterial walls comprising the extracellular matrix and elastin. In addition, these cells are constantly subjected to shear stresses due to fluid flow within the vessels. The combination of tensions and shear stresses exerted on the endothelial cells influence their proliferation and monolayer formation through biochemical cues. ECFCs cultured on flat 2D substrates (FIG. 6) and in microchannels (FIGS. 7A-7C) in 5, 10 and 15% GelMA hydrogels showed increased proliferation and a greater tendency to form monolayers in gels of higher stiffness. Previous studies on the effect of substrate stiffness on endothelial cells have observed that soft substrates were more conducive to microvascular network formation, while stiffer matrices supported endothelial cell proliferation, individual cell spreading and hence monolayer formation. The disclosed results (FIGS. 4-6) suggest that relatively stiffer (12 kPa) GelMA hydrogels enhance both OD21 cell behavior as well as endothelial monolayer formation by ECFCs.

Example 13—Fabrication of Pre-Vascularized Hydrogel Scaffolds for Pulp Regeneration In Vitro In order to test the above observations in hydrogel scaffolds with physiological dimensions and constraints, a full-length root canal model was used. A microchannel was formed in cell-laden GelMA hydrogel tissue constructs to ensure that a functional vascular-like conduit could be formed through the engineered pulp scaffolds from the onset of the regenerative process. Without being bound by theory, this conduit ensures that oxygen/nutrient diffusion and waste removal, which is further promoted by the length of the scaffolds during the remodeling process. Moreover, the fabricated microchannel is believed to provide a path for the migration of host cells to home into the scaffold structure from the root apex.

Figure 8:
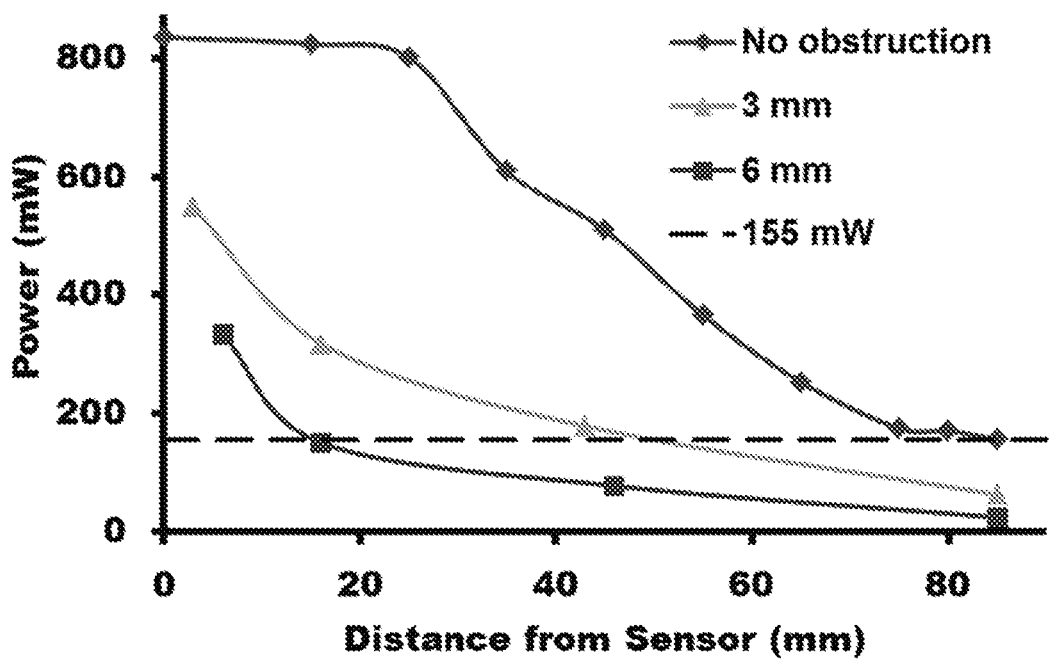
FIG. 8 represents the power (mW) and distance from sensor (mm) curves for curing tested hydrogels.

Extracted, endodontically prepared, single-rooted human pre-molars were obtained and an agarose fiber positioned across the entire length of root canal, traversing from the apex to the cervix. A cell-laden 15% GelMA hydrogel precursor was injected up to 3 mm of the root length and exposed the tooth exposed to UV light for 30 s. The hydrogel precursor injection and curing process was repeated 3 times, to ensure thorough photo-polymerization of the material (FIG. 8) along the entire root canal, while ensuring that the cells were exposed to the same intensity of UV light that we determined to be non-cytotoxic in the above described cell-viability experiments.

Figure 9A:
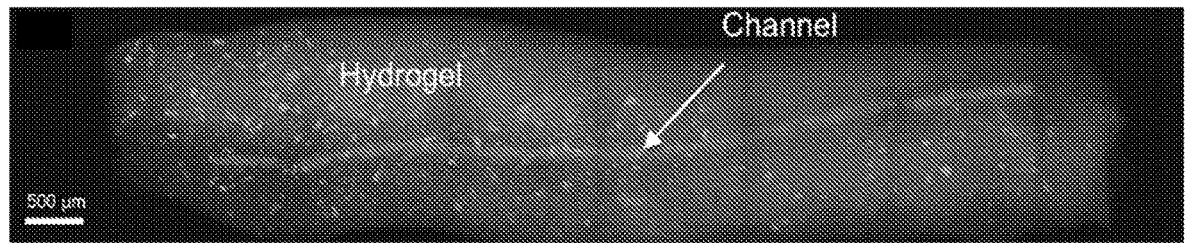
FIGS. 9A-9D depict channels formed in tested hydrogels.
Figure 9B:
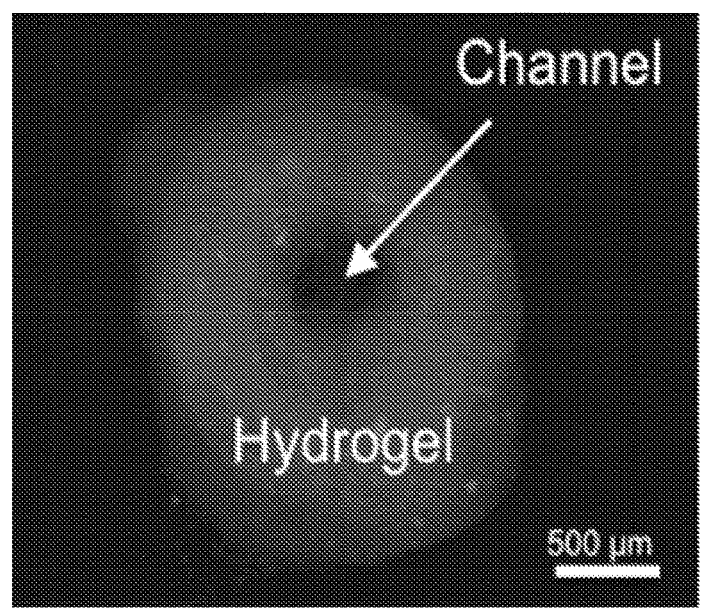
Figure 9C:
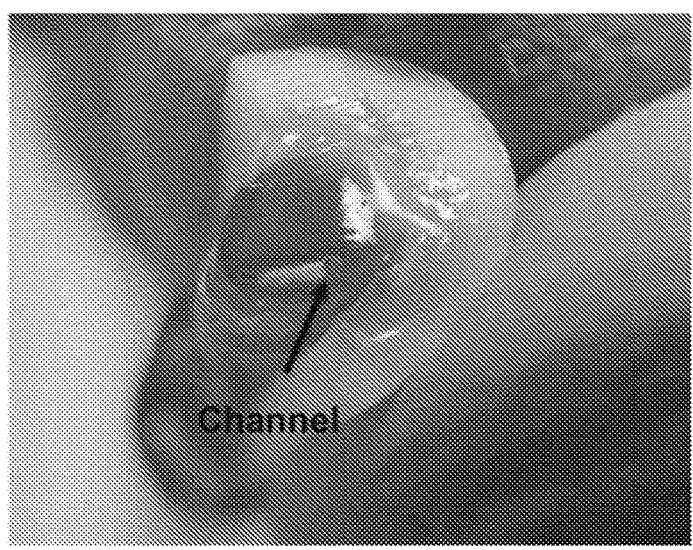
Figure 9D:
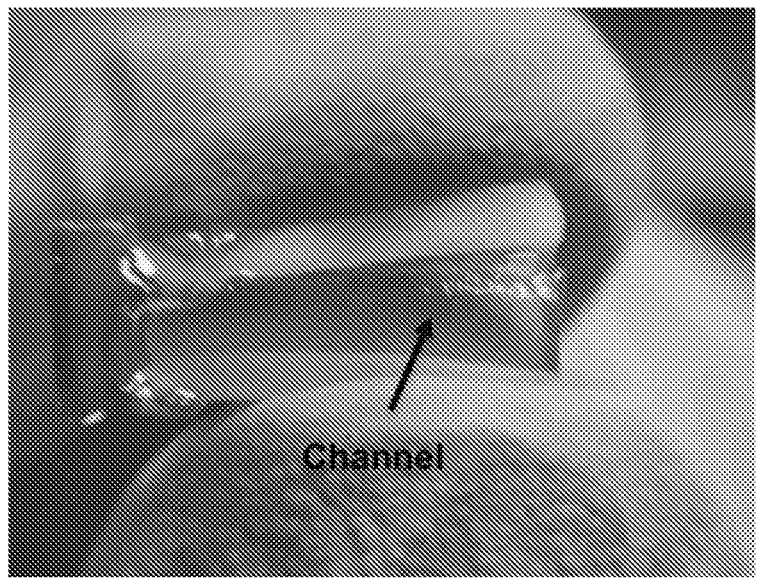
Figure 10A:
FIGS. 10A-10D provide images of a microchannel formed in a tested hydrogel through standard photography and phase contrast microscopy.
Figure 10B:
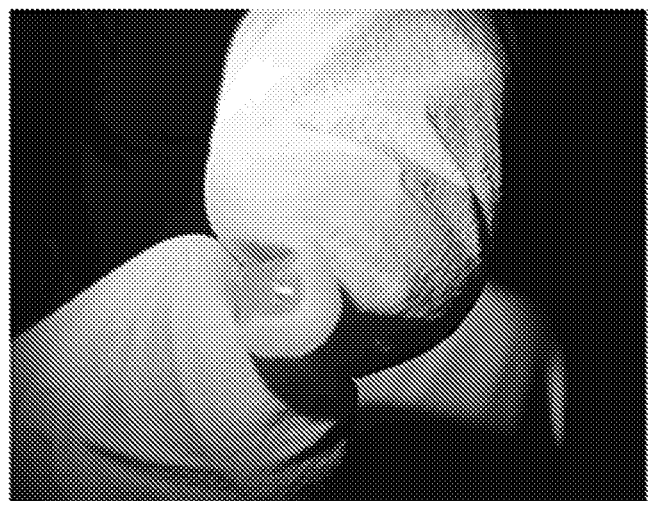
Figure 10C:
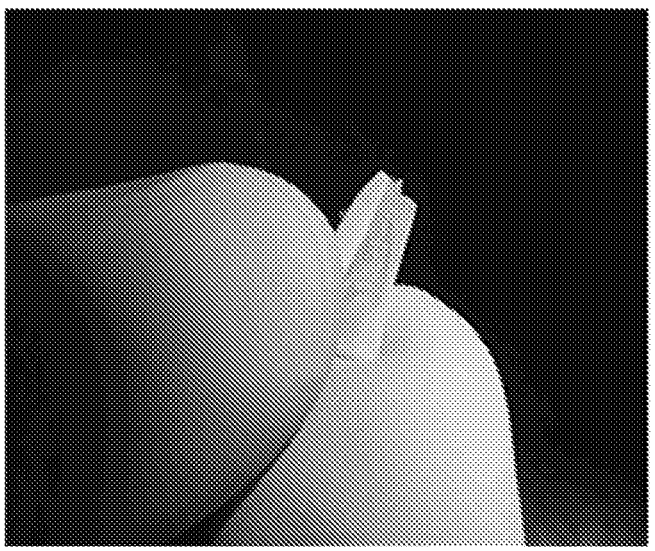
Figure 10D:
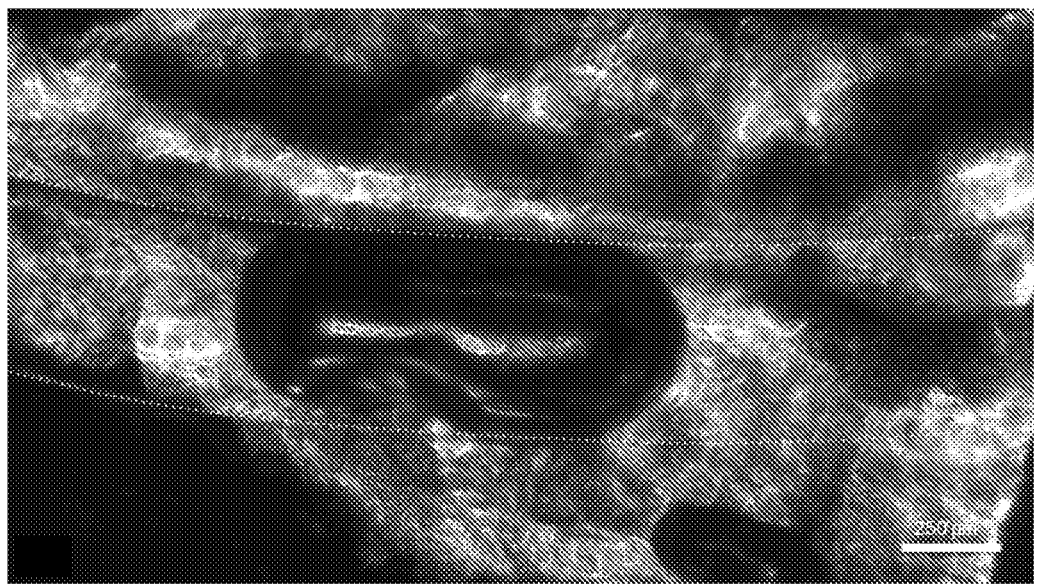

FIG. 9 shows representative fluorescent microscope images and photographs of a hydrogel tissue construct retrieved from an endodontically prepared tooth, after perfusion of the fabricated microchannel with a red-fluorescent particle solution (FIGS. 9A-9B) or a red dye (FIGS. 9C-9D). The longitudinal and transversal position of the microchannels along the tooth are visible. FIG. 10 depicts photographs of an intact cell-laden hydrogel tissue construct containing a microchannel retrieved from a similarly endodontically prepared tooth after 7 days (FIGS. 10A-10B) in culture and a phase contrast microscope image (FIG. 10) where densely cellularized structures are visible both within and outside the microchannel.

Figure 11A:
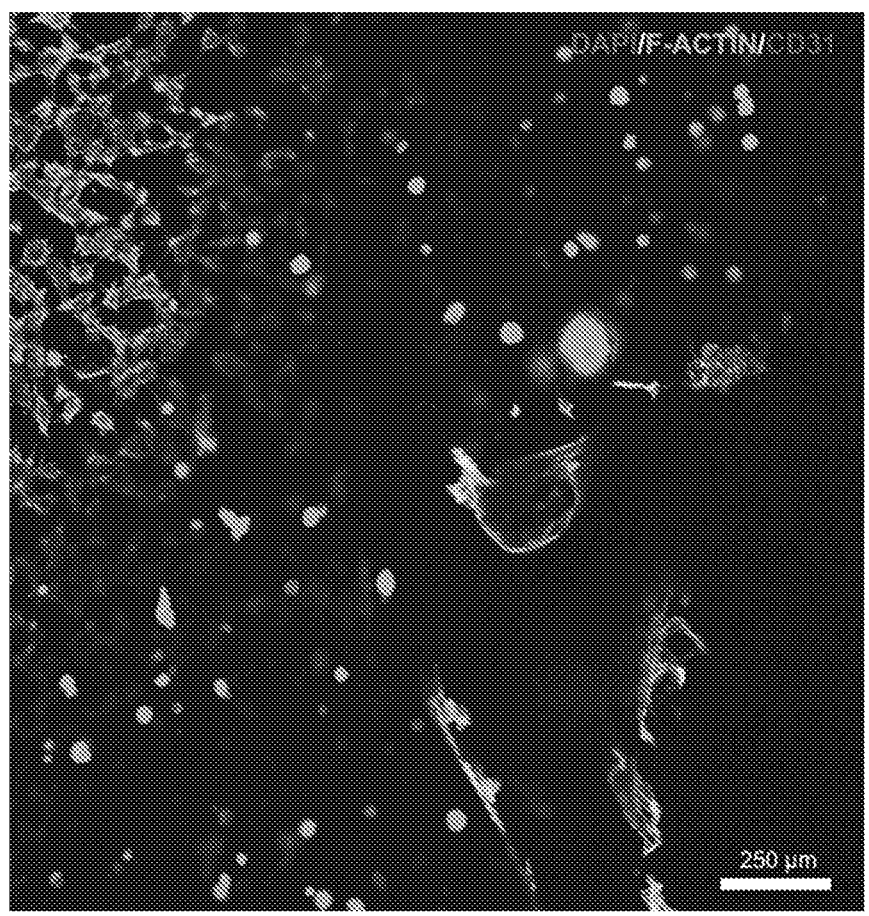
FIGS. 11A-11B show OD21 cells within tested hydrogels in close proximity to dentin walls (11A) and formed microchannel (11B).
Figure 11B:
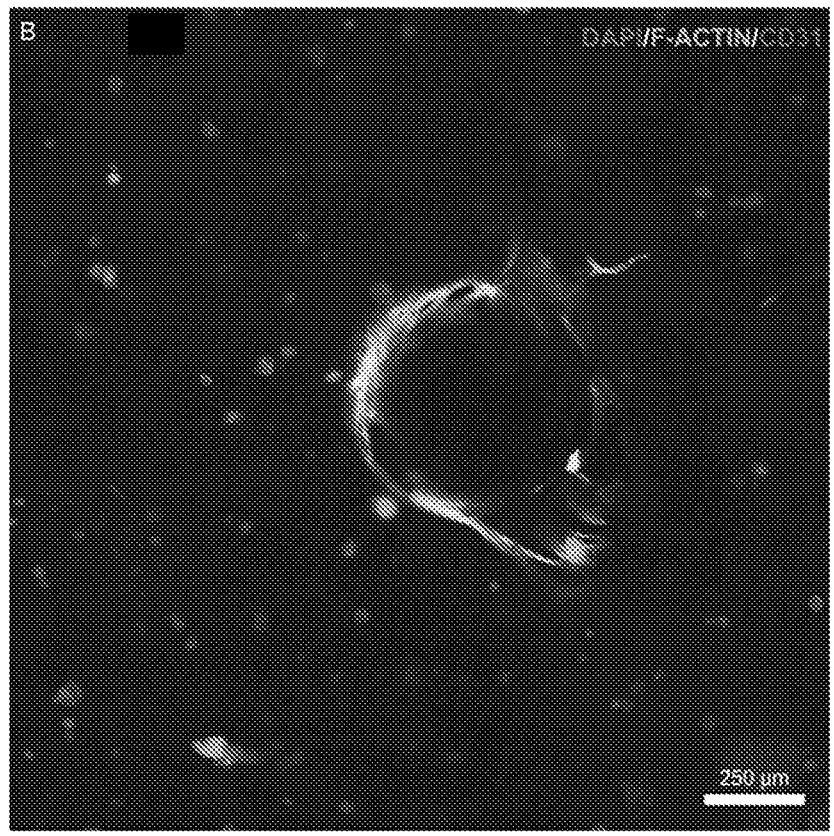
Figure 12A:
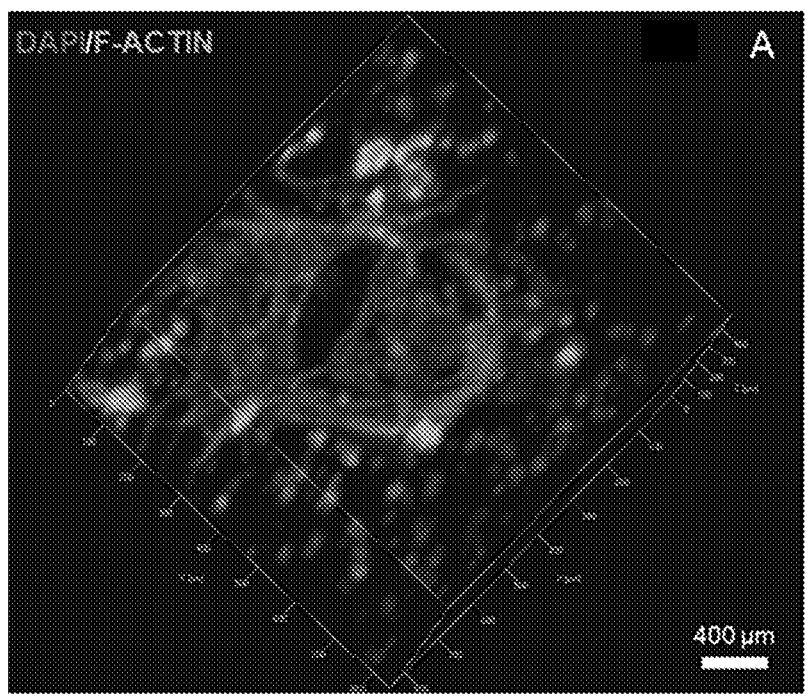
FIGS. 12A-12C provide a confocal image of an endothelial monolayer along the circumference of a hydrogel microchannel.
Figure 12B:
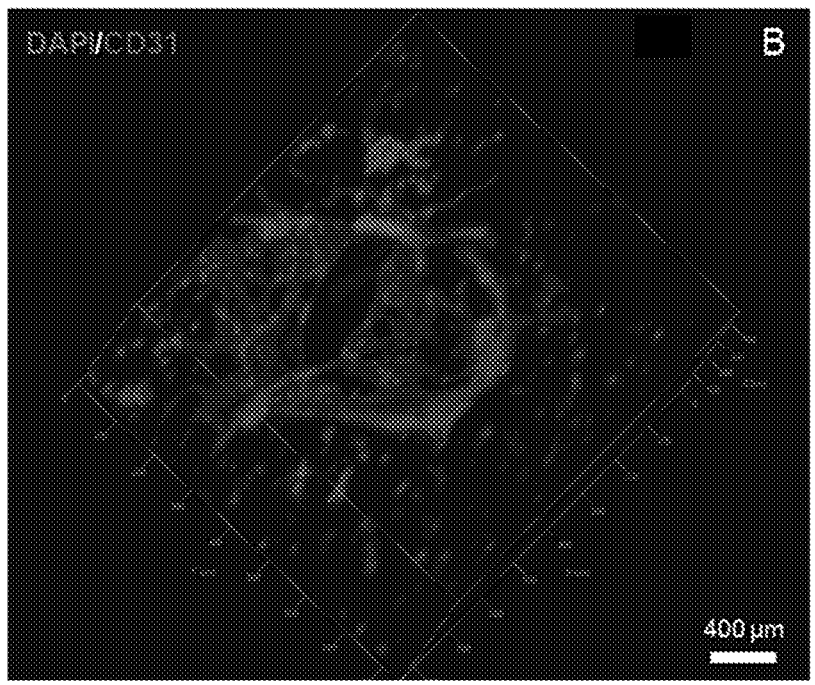
Figure 12C:
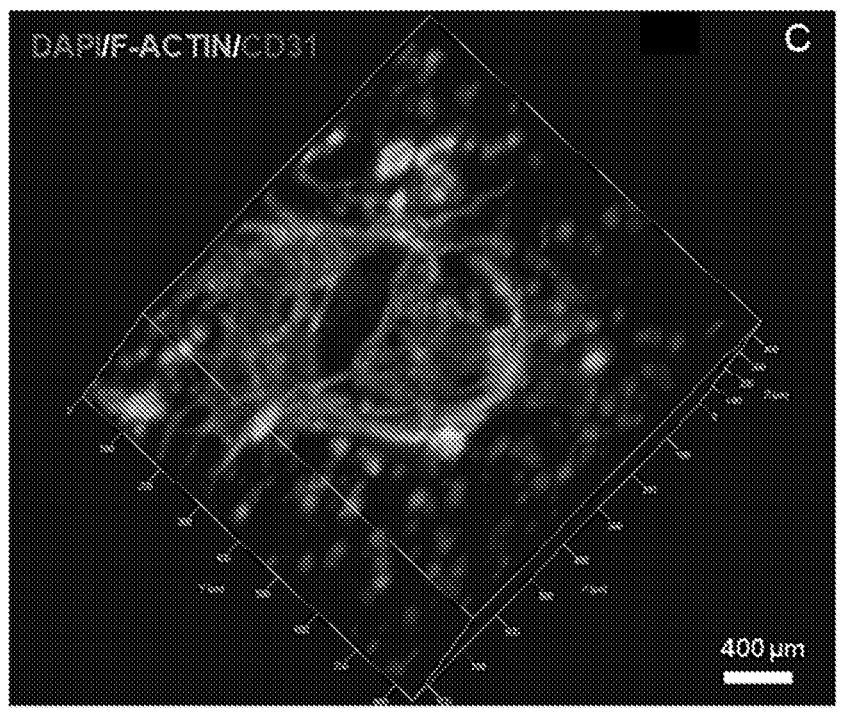
Figure 12D:
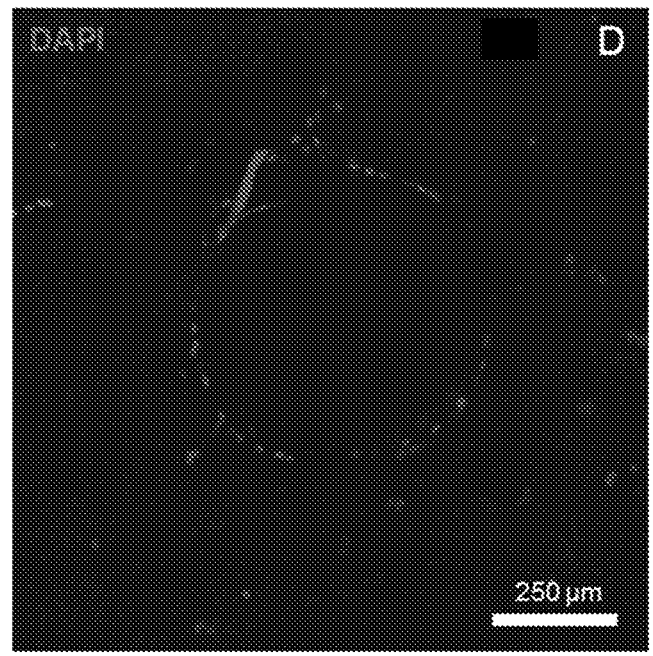
FIGS. 12D-12G show endothelial cell sprouting after monolayer formation.
Figure 12E:
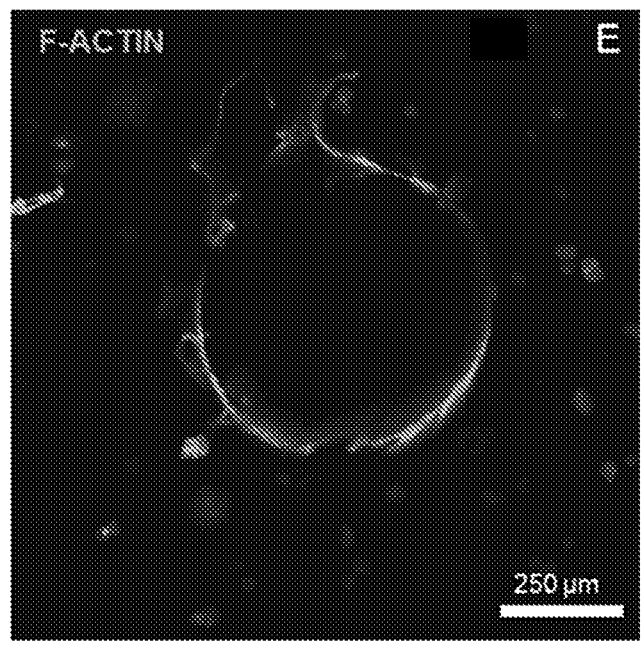
Figure 12F:
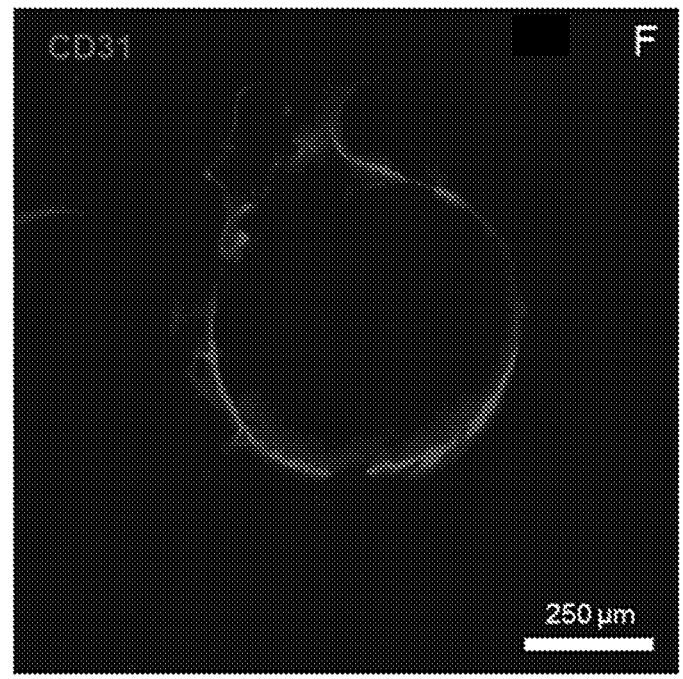
Figure 12G:
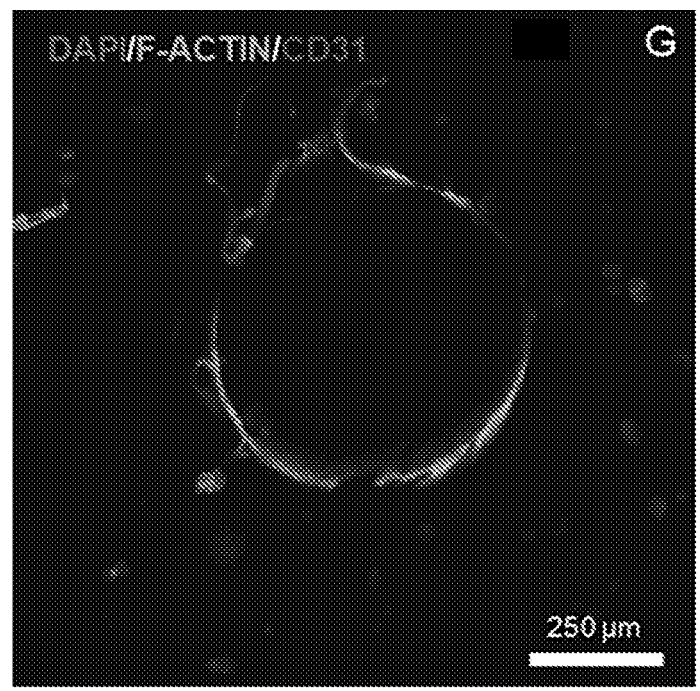

Confocal microscopy images of scaffolds retrieved from the prepared teeth showed that OD21 cells encapsulated within the hydrogels tended to have higher spreading in close proximity to the dentin walls (FIG. 11A) than around the microchannels (FIG. 11B), despite the visible presence of spread ECFCs in the form of endothelial sprouts in those areas. This further suggests the preference of OD21 cells for substrates of higher stiffness, as noted earlier. FIGS. 12A-12C show a confocal image of the endothelial monolayer along the circumference of the microchannel in a section of the channel. CD31 is highly expressed in these cells, indicative of tight cell-cell junctions. Cross-sectional views of these channels (FIGS. 12D-12G) also show endothelial cell sprouting in certain locations indicative of activation of angiogenic events through cell-cell junctions after monolayer formation as well as the dentin matrix components which have been shown to stimulate angiogenic activity at relatively low concentrations.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

Also provided herein are methods and compositions in which light-emitting diode (LED) photopolymerized gelatin methacryloyl hydrogels (GelMA), encapsulated with stem cells from the apical papilla (SCAP) and human umbilical vein endothelial cells (HUVECs), promote vasculature network formation as a function of hydrogel physical and mechanical properties, as well as total cell density. Lithium acylphosphinate (LAP) was used as the photoinitiator in concentrations of 0.05, 0.075, 0.1% (w/v). GelMA hydrogel precursors of 5% (w/v) were encapsulated with co-cultures of SCAPs and HUVECs at different cell densities (1×, 5× and $10\times10^6$ cells/ml) and photocrosslinked for 5 s. Results suggested that the compressive modulus of GelMA hydrogels increased as a function of LAP concentration, and had a maximum stiffness of 3.2 kPa. Hydrogel pore size decreased consistently with PI concentration and varied from approximately 20<m (0.1% LAP) to about 50<m (0.05% LAP). GelMA hydrogels photopolymerized using 0.05 or 0.075% LAP, which had an average of 1.5 and 1.6 kPa of elastic modulus respectively, had the most efficient vasculature formation after 5 days, and these results were further enhanced when the highest cell density ($10\times10^6$ cells/ml) was used. Immunofluorescence images showed that SCAP cells spread in close contact with endothelial networks and expressed alpha smooth muscle actin ($\alpha$SMA), which is suggestive of their differentiation into pericyte-like cells. $\alpha$SMA expression was also apparently higher in hydrogels polymerized with 0.05% LAP and $10\times10^6$ cells/ml. In conclusion, photopolymerization of GelMA hydrogels using an LED-light source can be an effective method for potential chair-side/in-situ procedures for engineering of vascularized tissue constructs in regenerative medicine.

Materials and Methods
Cell Culture

SCAPs were donated by Dr. Anibal Diogenes (University of Texas) and were obtained as previously published (Fairbanks et al., *Biomaterials* 2009, 30 (35), 6702-7). Briefly, fragments of the apical papilla from third molars were digested by incubation with a solution of 3 mg/ml collagenase type I (Worthlington Biomedical, Lakewood, N.J.) and 4 mg/ml dispase (Sigma, St Louis, Mo.) for 30 minutes. Cells were centrifuged (1500 rpm, 2 min) and re-suspended in alpha-minimum essential medium (a-MEM; Gibco, Grand Island, N.Y.) supplemented with 1× L-glutamine (Gibco), 10% fetal bovine, penicillin (100 U/ml; Gibco), and streptomycin (100 mg/ml; Gibco). Cells were seeded and expanded to 70%-80% confluence and used up to passage 10. GFP expressing HUVECs (cAP-0001GFP, Angioproteomie, USA) were expanded up to passage 6 in endothelial cell growth medium (EGM2, Lonza, USA) with EGM2 BulletKit (cc3162, Lonza, USA) on 0.1% gelatin coated substrates. All cells were cultured in humidified 5% CO2 at 37° C., and were cryopreserved in 10% dimethylsulfoxide (DMSO) in appropriate culture media until use.

Gelatin Methacryloyl (GelMA) Synthesis

The synthesis of GelMA was performed as described previously (Nichol et al., Biomaterials 2010, 31 (21), 5536-5544). In brief, porcine skin type A gelatin (10% w/v) (Sigma, St Louis, Mo., USA) was dissolved in 50° C. Dulbecco's phosphate buffered saline (DPBS, Sigma). 8% (v/v) methacrylic anhydride (Sigma) was added to the solution dropwise, allowing the reaction to proceed for 2 hours, and subsequently stopping it with a 5× dilution of DPBS. The solution was dialyzed against distilled water using a 12-14 kDa dialysis tubing at 45±5° C. for five days with two water changes per day. The resulting macromer was then lyophilized for 5 days and stored at room temperature until further use.

Physical and Mechanical Properties

GelMA macromer at a concentration of 10% (w/v) was dissolved in DPBS with lithium acylphosphinate (LAP, Tokyo Chemical Industry, L0290) photoinitiator of 0.05, 0.075, 0.1% (w/v). GelMA hydrogels were fabricated by dispensing the gel precursors into Poly(dimethylsiloxane) (PDMS, Sigma) molds measuring 5 mm in diameter and 2.5 mm in height and exposing the samples to a visible LED light using a clinically available light curing device (VALO, Ultradent) which emits light in the visible range between 395 and 480 nm through a 10.5 mm diameter curing tip. Hydrogels were photocured using a power of 1650 mW/cm2 for 5 s. Hydrogel pore structure and morphology were analyzed via scanning electron microscopy (SEM), for which hydrogels (n=3) were cross-sectioned, flash frozen in liquid nitrogen, lyophilized overnight (Labconco, Freezone 4.5) and then coated with gold/palladium prior to imaging using a FEI Quanta 200 SEM at 20.0 kV. Pore size and total area of porosity were quantified using ImageJ. Hydrogel degradation was determined by incubating GelMA hydrogel disks (n=4) for 2, 5, 8 and 16 hours at 37° C. in a 1 U/ml collagenase solution (MP Biomedical). After incubation, the non-degraded hydrogel fragments were retrieved and lyophilized overnight. Degradation percentage was determined by calculating the weight ratio of degraded versus intact hydrogel samples at each time point. Compressive modulus of the hydrogel samples was determined using an unconfined compression testing method on a universal mechanical testing machine (MTS Criterion), at a loading rate of 1 mm/min, and determining the slope of the linear region corresponding to 0%-10% strain (n=4).

Cell Encapsulation—Effect of LAP Concentration and Cell Seeding Density

For quantification of SCAPs and HUVECs response as a function of hydrogel physical properties, cells were trypsinized and counted using Countess™ IIFL automated cell counter (Life Technologies), and re-suspended in 10% GelMA hydrogel prepolymer at a cell density of $5\times10^6$ cells/ml in a 1:4 cell ratio. In order to adjust the hydrogel physical and mechanical properties without interfering with the density of cell adhesion ligands naturally present in gelatin, the hydrogel prepolymer was mixed in DPBS containing either 0.05, 0.075 or 0.1% (w/v) LAP. Cell-laden hydrogel constructs were fabricated by dispensing 5<1 of a cell-laden hydrogel precursor on plastic Petri dish, and compressing the cell-laden droplet with a TMSPMA ([3-(Methacryloyloxy)propyl]trimethoxysilane, Sigma) coated glass slide supported by two parallel cover slips, to form 100<m thick GelMA constructs, as described previously (Athirasala et al., Scientific Reports, Article No. 3323 (2017). Photocrosslinking was achieved by exposing all samples to light for 5 seconds, as explained above (N=8). To test the effect of cell seeding density, SCAP and HUVECs at 1:4 cell ratio were re-suspended in the GelMA hydrogel prepolymer (10%, 0.075% PI), at densities of $1\times10^6$ cells/ml, $5\times10^6$ cells/ml and $10\times10^6$ cells/ml. Samples were photopolymerized as above. Cell-laden hydrogel constructs were cultured in endothelial cell growth medium (EGM2, Lonza, USA) supplemented with EGM2 BulletKit (cc-3162, Lonza, USA) for 7 days, and the medium was changed every two days.

Vascular Network Analysis

Analysis of vasculature formation was performed by imaging the GFP expressing HUVECs in the cell-laden hydrogels at different time points using an automated fluorescence microscope (EVOS FL Auto, Life Technologies). Images were processed using Fiji (ImageJ, NIH), and vasculature formation was quantified using AngioTool (NIH) following a pre-optimized routine of image segmentation, skeletonization and determination of default thresholds for vessel diameter, signal intensity, and removal of small particles. Vessels were compared as a function of vessel percent area, total vessel length, average vessel length, and vascular branching index.

Immunofluorescence

Cell-laden hydrogels were fixed in paraformaldehyde (4%) and permeabilized with 0.1% Triton X-100 in DPBS for 25 min. The hydrogels were then blocked with bovine serum albumin (BSA) (1.5%, Sigma-Aldrich) in DPBS for 1 h. After washing with PBS, samples were incubated with primary mouse monoclonal antibody (anti-$\alpha$-SMA, Abcam, 1:400) overnight at 4° C. Samples were washed with PBS and incubated with secondary antibody (1:250, goat anti-mouse Alexa Fluor 555, Invitrogen) for 3 h. This was followed by rinsing in 0.1% PBS, staining of the nuclei using a NucBlue staining kit (ThermoFisher Scientific, Waltham, Mass. USA) for 20 min at 37° C. Samples were examined using a fluorescence microscope (EVOS FL Auto, Life Technologies) and images were further processed using Fiji (ImageJ, NIH).

Data Analysis

Statistical analysis was performed using GraphPad Prism 6. The values represent averages±standard deviations. A two-way ANOVA followed by Tukey post-hoc test ($\alpha$=0.05) was used to analyze the differences between different LAP concentrations, and cell densities.

Results

Physical and Mechanical Properties of LED-Light Photopolymerized GelMA

Notably, the compressive modulus only increased significantly when the LAP photoinitiator concentration was increased from either 0.05% (1.5±0.3 kPa) or 0.075% (1.6±0.4 kPa) to 0.1% (3.1±0.6 kPa) (p<0.01 and <0.05, respectively), with no significant increase from 0.05 to 0.075%. The percentage of hydrogel mass left after 2 hours of induced degradation was 77%, 81% and 85% for 0.05, 0.075 and 0.1% GelMA hydrogels, respectively. After 8 hours, GelMA hydrogels photopolymerized with 0.05, 0.075 and 0.1% PI degraded 72%, 69% and 63% respectively, where the hydrogels with 0.1% PI concentration had significantly higher resistance against degradation than the 0.075% (p<0.001) and 0.05% (p<0.0001) groups. After 16 hours, all GelMA hydrogel groups were completely degraded. GelMA hydrogels were photopolymerized using 0.05, 0.075 and 0.1% PI concentrations. While 0.05% PI concentration induced the greater pore sizes (approximately 50<m), 0.1% had visibly lower porosity, which was confirmed by the quantification of pore size, where 0.1% PI lead to a nearly one-fold decrease in pore size compared to 0.05% PI.

Figure 13:
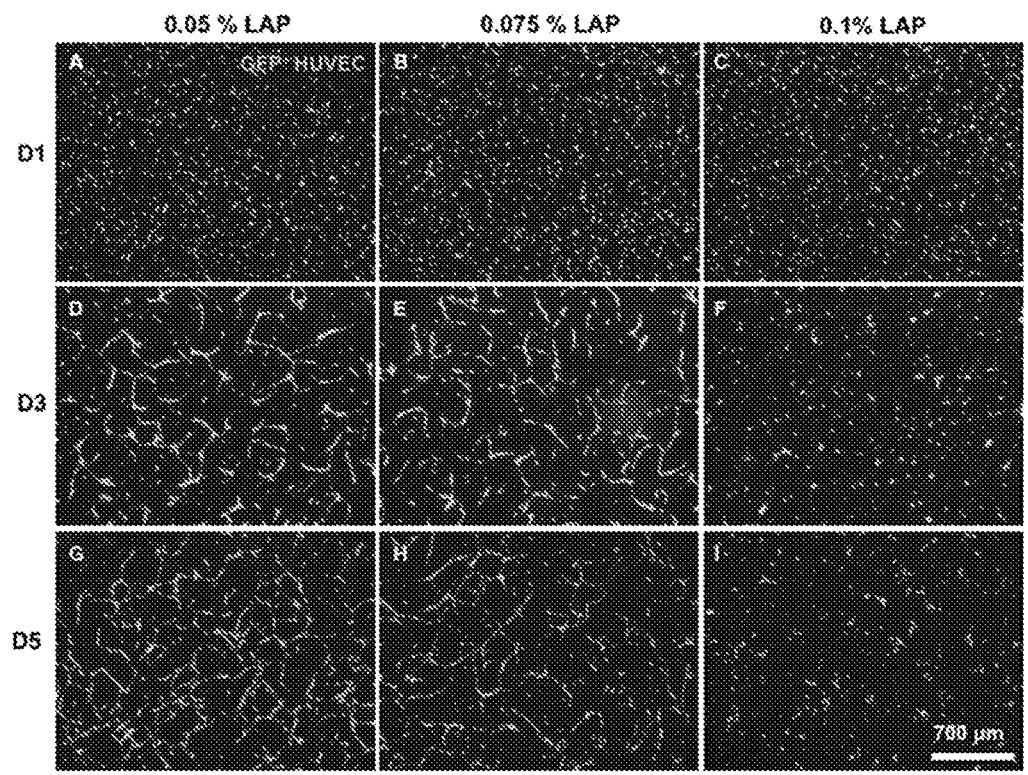
FIG. 13 shows morphology of GFP-expressing HUVECs co-cultured with SCAP in different hydrogel photoinitiator (PI) concentrations.

Effect of LAP Concentration on Vascular Network Formation and SCAP Differentiation In order to determine the influence of hydrogel physical and mechanical properties on the formation of vascular networks in cell-laden GelMA hydrogels, we compared the morphology of GFP expressing HUVECs cocultured with SCAP (unstained) for 1, 3 and 5 days in hydrogels with different PI concentrations (FIG. 13). The images show that HUVECs had comparable behavior in the first 48 h of culture, with no visible spreading or network formation (FIG. 13a-c). After 72 h, only hydrogels with 0.05 and 0.075% PI had visible and well-defined networks across the sample (FIG. 13d-e), while 0.1% PI had no discernible vascular networks (FIG. 13O. By day 5 (FIG. 13g-l), both GelMA hydrogels with 0.05 and 0.075% PI had sustained vascular networks, while 0.1% PI failed to form well-defined vascular capillaries. Quantification of the networks after initial vessel-like structures were formed on day 3 (FIG. 14) show that GelMA hydrogels with low concentration of LAP (0.05% and 0.075%) had significantly higher vessel percent area than 0.1% LAP on both days 3 and 5 (p<0.0001). No significant differences were observed between 0.05% and 0.075% LAP at days 3 or 5. Quantification of total vessel length showed a similar trend, where 0.05% and 0.075% were consistently higher than 0.1% PI on days 3 and 5 (p<0.0001 and p<0.01, respectively). The endothelial networks reached their maximum length and branching index on day 5, where significant differences were observed between 0.05% vs 0.075% LAP and 0.075% and 0.1% LAP. $\alpha$-smooth muscle actin ($\alpha$-SMA)-expressing SCAPs were localized in close proximity to the vessel-like structures, suggesting direct cell-cell interactions and perivascular coverage; both of which are consistent with a pericyte-like phenotype. Fluorescence images of cells on day 7 showed a strong expression of $\alpha$-SMA in all three groups, and consistent perivascular coverage was observed in the 0.05%, 0.075% LAP GelMA constructs. 0.1% LAP GelMA constructs, on the other hand, showed comparatively lower expression and scant association with GFP-expressing HUVECs, which failed to form vascular networks.

Effect of Cell Density on Vascular Network Formation and SCAP Differentiation

Figure 15:
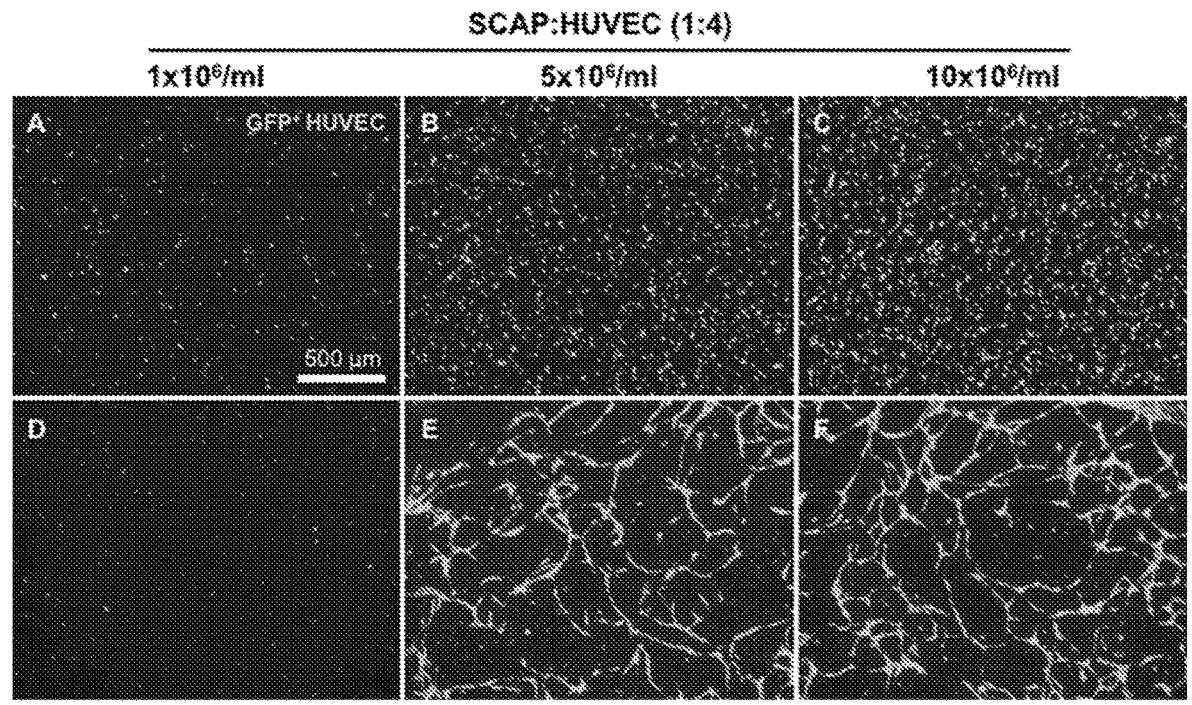
FIG. 15 demonstrates vascular networks achieved through 3 different cell density cultures.

After determining that hydrogels of lower stiffness and LAP concentration (0.05 and 0.075%) promoted improved vessel-like network formation, we studied the effect of cell density on vascularization of LED photocrosslinked hydrogels containing 0.75% LAP. FIG. 15 shows that cocultures of SCAPs and HUVECs at low cell density ($1 \times 10^6$ cells/ml) did not form vascular networks, whereas a robust vasculature was consistently present in samples cultured with either $5 \times 10^6$, or $10 \times 10^6$ cells/ml, thus suggesting that vascular network formation is significantly improved as a function of cell-cell contact or proximity. Interestingly, vascular networks only formed when HUVECs were co-cultured with SCAPs, and HUVECs alone did not form vessels after at least 7 days, indicating a critical effect of SCAP on HUVECs during vessel-like network formation.

Figure 16:
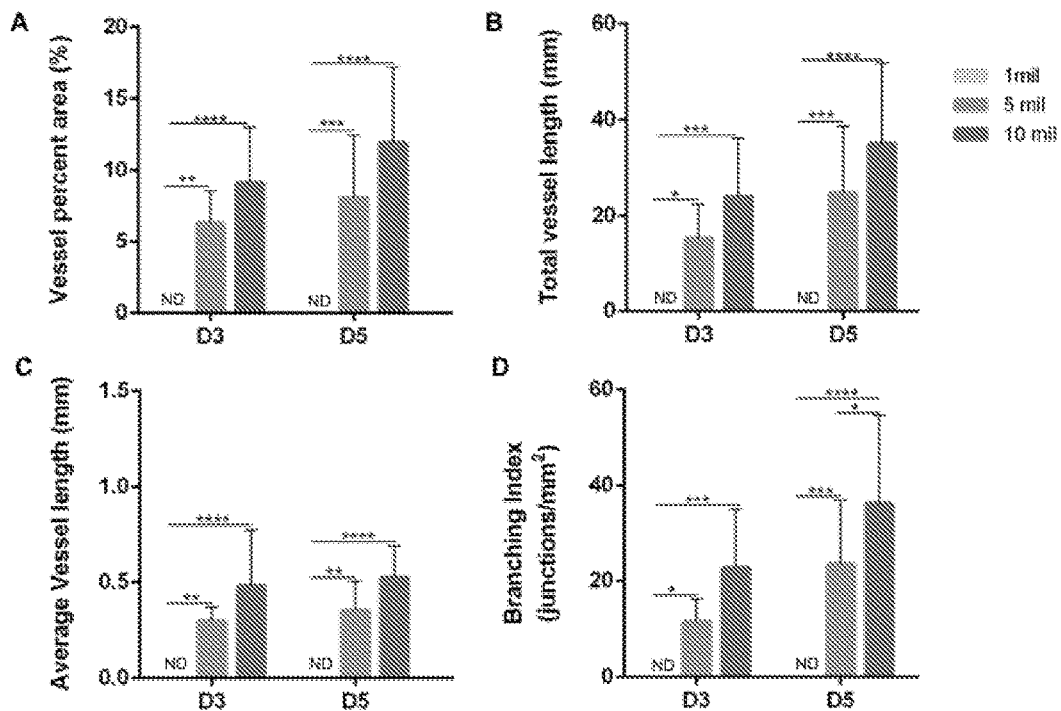
FIG. 16 quantifies vascular network formation based on initial cell densities.
Figure 17:
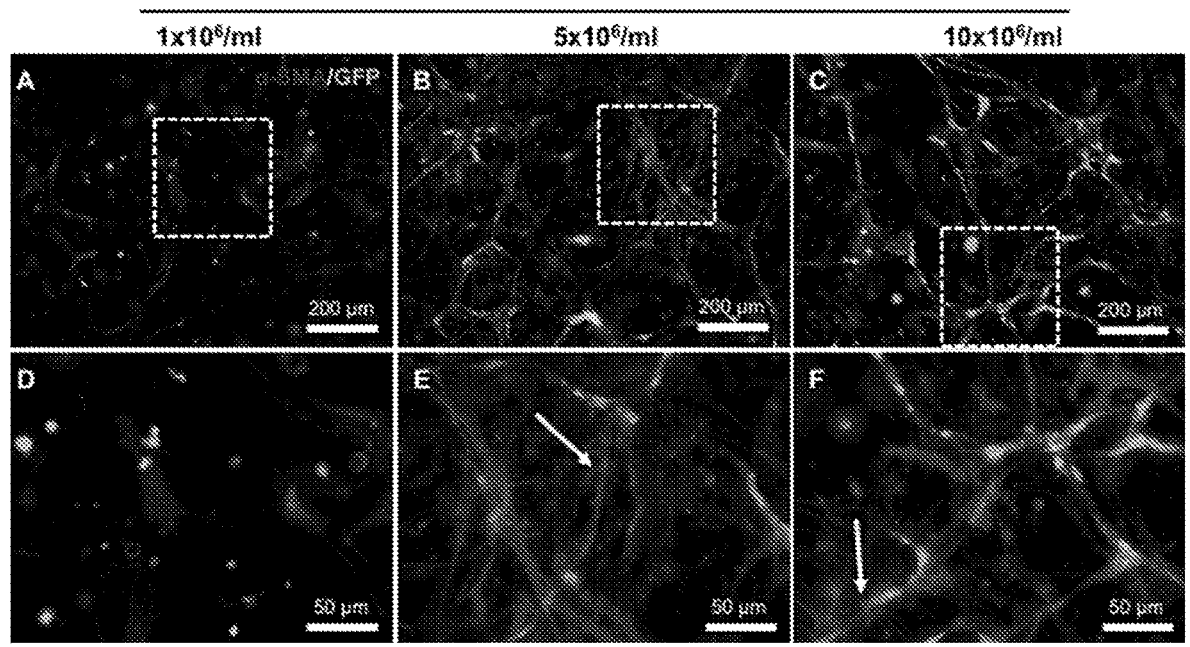
FIG. 17 depicts perivascular coverage observed in differing concentrations of co-cultured cells.

FIG. 16 shows the quantification of vascular network formation at different cell densities. GelMA hydrogels encapsulated with SCAPs and HUVECs at cell densities of $5 \times 10^6$ and $10 \times 10^6$ cells/ml formed interconnected vascular networks with significantly higher vessel percent area, total vessel length, average vessel length, and branching index than co-cultures at a cell density of $1 \times 10^6$ cells/ml on days 3 and 5, which were non-detectable at all time points. No significant differences were found for the comparison of average vessel percent area, total vessel length, average vessel length, between $5 \times 10^6$ and $10 \times 10^6$ on days 3 and 5; the only significant difference between these two groups was seen after 5 days with regards to branching index (FIG. 16d). Lastly, FIG. 17 shows that co-cultures of SCAPs and HUVECs at low cell density did not form vessel-like networks, while SCAPs still expressed a comparatively low level of α-SMA (FIG. 17a-d). Perivascular coverage was visibly more robust in the 10×10$^6$ cells/ml samples (FIG. 17 c-f) than in those with 5×10$^6$ or 1×10$^6$ cells/ml (FIG. 17be).

The development of new vascularized hydrogels in-vitro is essential for tissue engineering. The formation of a functional vascular system prior to implantation is thought to enhance oxygen and nutrient delivery to the core of the scaffolds from the onset of the remodeling process upon implantation (Bae et al., Sci Transl Med 2012, 4(160), 160ps23). Similarly, waste products from metabolically active cells in the core of the construct can be more easily removed. Furthermore, increasing the cell-cell interactions that take place during vasculature formation is thought to increase the secretion of paracrine and angiocrine factors that orchestrate the homing of host vessels towards the growing vasculature, thus enabling vessel-vessel anastomosis (Barabaschi et al, Adv Exp Med Biol 2015, 881, 79-94). Here we characterize several of the microenvironmental parameters that enhance the early steps of vasculature formation process in-vitro in LED-light polymerized cell-laden hydrogels. We show that 3D co-cultures of SCAPs and HUVECs formed extensive vessellike networks in vitro as a function of photoinitiator concentration, hydrogel physical and mechanical properties, and cell density.

Hydrogel photopolymerization has been widely used for regenerative applications. The majority of hydrogel light curing strategies, however, has relied on photoinitiators that are activated by light in the UV range (Annabi et al, Advanced Materials (Deerfield Beach, Fla.) 2014, 26(1), 85-123). UV light has been shown to generate considerable levels of reactive oxygen species that can cause endogenous DNA oxidation, immunosuppression and accelerated tissue aging. Hydrogel photopolymerization using visible light, therefore, has been proposed as an interesting alternative with potentially less translational hurdles. Several photoinitiators that are labile to light in the visible range have been used for hydrogel photopolymerization, including camphoroquinone, fluorescein and riboflavin. However, these methods have required prolonged irradiation times to obtain adequate mechanical properties, which consequently leads to potential toxic effects to encapsulated cells. More recently Noshadi et al. proposed the use of Eosin Y as a photoinitiator to be used together with triethanolamine and N-vinylcaprolactam as co-initiators and co-monomers, respectively, for engineering of cell-laden hydrogels cured using visible light (Noshadi et al., Biomater Sci 2017, 5(10), 2093-2105). This attempt has resulted in efficient hydrogel photopolymerization with a wide range of mechanical properties (5-56.5 kPa) and high cell-viability (>80% after 5 days), despite the 180 s of light exposure. Here we demonstrate that cell-laden GelMA hydrogels can be photopolymerized using an FDA-approved and clinically available LED blue-light source (395-405 nm) that requires a maximum of 5 s to induce hydrogel gelation. This represents a substantial leap in performance of visible light-polymerized cell-laden hydrogels. Moreover, we demonstrate that these hydrogels can be used for engineering of stem-cell supported vasculature networks in 3D in as little as 3 days of cell culture in-vitro, which can have significant implications for regeneration of vascularized tissues in-situ.

Figure 14:
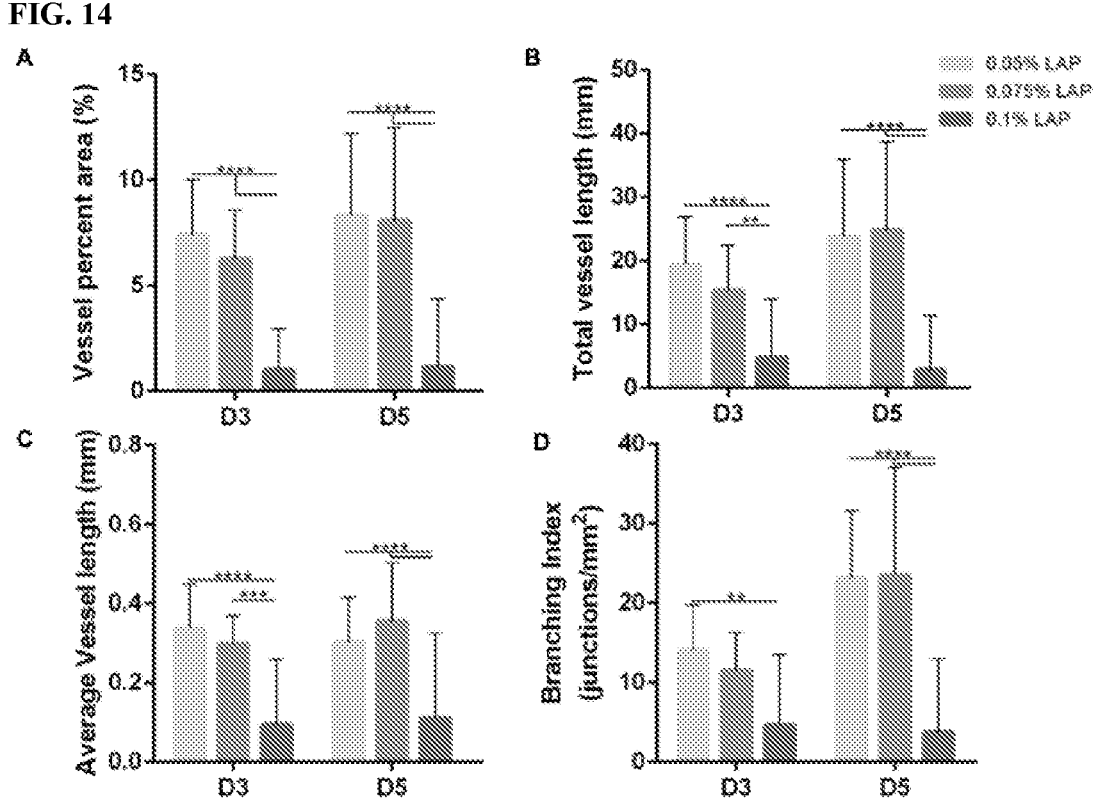
FIG. 14 provides quantification of vascular networks in hydrogels with varying LAP %.

It is well known that co-cultures of EC and stem cells can be used to recapitulate aspects of vasculogenesis in-vitro (Chen et al., Advanced Functional Materials 2012, 22(10), 2027-2039, and Rao et al., Angiogenesis 2012, 15(2), 253-264). Stem cells are known to stimulate ECs to form vessel-like structures, which mature as the stem cells themselves differentiate into a pericyte-like phenotype. In our study, the ability of cells to form vessel-like networks decreased drastically when the LAP concentration was increased from 0.075 to 0.1% (FIG. 13). SCAPs and HUVECs encapsulated in 5% GelMA with 0.05% and 0.075% LAP constructs generated 3D interconnected vascular networks with significantly higher vessel percent area, total vessel length, average vessel length, and branching index than 0.1% LAP (FIG. 14). We postulate that these results can be explained by the fact that the higher concentration of LAP increased the stiffness of the GelMA hydrogels beyond the threshold at which ECs and SCAPs were able to effectively remodel the gels. Both ECs and SCAPs are known to have a contractile phenotype that is driven by specific mechanotransduction pathways (Engler et al., Cell 2006, 126(4), 677-689), in which the local microenvironment properties, especially matrix stiffness, are known to influence the ability of these cells to regulate their physiologic response. Chen et al. reported an increase of the compressive modulus of GelMA hydrogels from 2 kPa to 4.5 kPa by varying the degree of methacrylation of gelatin from 1M to 10M, respectively. They showed that 2 kPa GelMA hydrogels formed robust vessels, whereas, 4.5 kPa GelMA hydrogels hampered the formation of vessel-like networks in co-culture of mesenchymal stem cells and ECs. This is in line with our observations, where the compressive modulus of our LED light photopolymerized GelMA hydrogels increased from 1.5 kPa to 3.1 kPa by increasing the LAP photoinitiator concentration increased from 0.05% to 0.1% LAP. No significant differences were observed between 0.05% and 0.075% LAP in terms of compressive modulus, and samples formed vessellike structures for both of these LAP concentrations despite a significant increase in degradation resistance and decrease in pore size. Therefore, independently of the method used to change matrix stiffness, results suggest that softer hydrogels promote vessel-like network formation, while stiffer hydrogels impair their formation in 3D whereas porosity and degradation seem to play a lesser role. Interestingly, our previous work on the culture of ECs on GelMA hydrogels of different elastic modulus suggested that ECs form monolayers significantly more efficiently when cultured in hydrogels of higher stiffness (>12 kPa), whereas GelMA hydrogels with compressive modulus below 5 kPa did not reach full confluence at all, either in flat substrates (Athirasala et al., Sci Rep 2017, 7(1), 3323) or in 3D printed microchannels (Athirasala et al., Scientific Reports, Article No. 3323 (2017), regardless of the culture time. These observations suggest that there may be substantially different mechanisms that regulate cell response when ECs are cultured in 2D and 3D. One qualifying factor, however, is that these studies involved increasing GelMA concentrations to increase stiffness and it may be argued that the paucity of adhesion sites in hydrogels of lower concentration (stiffness) may have undermined monolayer formation. Identifying the precise conditions that promote vasculature formation in cell-laden hydrogels and simultaneously enable monolayer formation in pre-formed microchannels, is an important question that remains to be addressed for future biomanufacturing approaches.

Our results also suggest that SCAPs were critically important for vessel-like network formation, and that increasing cell density promoted robust vessel-like network formation (FIG. 15). Vascular capillaries contain distinct lumens that are formed by the fusion of EC intracellular vacuoles during the process of vasculogenesis, and such a process is dependent on the presence of stem cells, which differentiate into perivascular cells occupying abluminal positions within the network (Chen et al., Advanced Functional Materials 2012, 22(10)2027-2039). Yuan et al reported that SCAP cocultured with HUVEC increased the number of vessel lengths, branching points, and SCAPs were located adjacent to the ECs, resembling the pericyte location in 2D. Similar results were also reported when ECs and mesenchymal stem cells were mono and co-cultured in 5% GelMA for 6 days. When cultured alone, ECs were unable to form vessel like structures and maintained round morphologies after 6 days, while MSCs were able to spread and proliferate. Similar results have been reported with different ECs and MSCs. Interestingly, our results suggest that not only the presence of a stem cell lineage is necessary for efficient vasculature formation, but also the total number of cells is critically important. Accordingly, when HUVECs were co-cultured with SCAPs at low density ($1\times10^6$ cells/ml) no discernible vessels were formed after at least 7 days (FIG. 17). Interestingly, SCAPs still expressed detectable levels of αSMA, which indicates that despite the lack of a robust vasculature, ECs may still exert sufficient paracrine and juxtacrine activity onto SCAPs to induce their differentiation into a pericyte-like lineage.

What is claimed is:

1. A method for treating decay of a tooth by promoting regeneration of vascularized dental pulp in a root canal in the tooth, the method comprising:
    positioning a fiber in the root canal of the tooth;
    filling at least a portion of the root canal with an unset hydrogel composition, such that the unset hydrogel composition contacts at least a portion of the fiber;
    setting the hydrogel composition, thereby forming a set hydrogel; and
    removing the fiber from the set hydrogel, thereby leaving a channel in the set hydrogel, the channel being sized to form a vascular-like conduit.

2. The method of claim 1, wherein the fiber ranges from about 100 μm to about 1 mm in diameter.

3. The method of claim 1, wherein the fiber ranges from about 450 to about 550 μm in diameter.

4. The method of claim 1, wherein the fiber comprises a pre-solidified agarose hydrogel.

5. The method of claim 1, wherein the fiber is removed by aspiration after the formation of the set hydrogel.

6. The method of claim 1, wherein the fiber is positioned within 500 μm of the center of the root canal.

7. The method of claim 1, wherein the unset hydrogel composition comprises a crosslinkable polymer.

8. The method of claim 7, wherein the crosslinkable polymer is gelatin methacroyl.

9. The method of claim 8, wherein unset hydrogel composition comprises the gelatin methacroyl in amount of at least 10% (w/v).

10. The method of claim 9, where the unset hydrogel composition comprises the gelatin methacroyl in an amount of at least 15% (w/v).

11. The method of claim 1, wherein the unset hydrogel composition is heated to a temperature around 50° C., thereby forming the set hydrogel.

12. The method of claim 1, wherein the unset hydrogel composition further comprises 2-hydroxy-4'-(2-hydroxyethoxy)-2-methylpropiophenone.

13. The method of claim 12, wherein the unset hydrogel composition comprises the 2-hydroxy-4'-(2-hydroxyethoxy)-2-methylpropiophenone in an amount of about 0.1% (w/v).

14. The method of claim 1, wherein the unset hydrogel composition further comprises lithium acylphosphinate.

15. The method of claim 14, wherein the unset hydrogel composition further comprises the lithium acylphosphinate at a concentration of from about 0.01% to about 1.5% (w/v).

16. The method of claim 15, wherein the unset hydrogel composition further comprises the lithium acylphosphinate at a concentration of from about 0.04 to about 0.08% (w/v).

17. The method of claim 1, wherein the unset hydrogel composition further comprises phosphate buffered saline.

18. The method of claim 1, wherein setting the unset hydrogel composition comprises photocrosslinking the crosslinkable hydrogel.

19. The method of claim 1, wherein the unset hydrogel composition further comprises cells selected from the group of odontoblasts, endothelial colony forming cells, multipotent stem cells, and pluripotent stem cells, and combinations thereof.

* * * * *